US008377654B2

(12) United States Patent
Gloger et al.

(10) Patent No.: US 8,377,654 B2
(45) Date of Patent: Feb. 19, 2013

(54) STABLE GALENIC FREEZE-DRIED PHARMACEUTICAL PREPARATION OF RECOMBINANT CARBOHYDRATE-BINDING POLYPEPTIDES

(75) Inventors: Oliver Gloger, Aachen (DE); Bernd W. Muller, Flintbeck (DE); Klaus Witthohn, Overath (DE)

(73) Assignee: Viscum AG, Bergisch-Gladbach (DE)

( * ) Notice: Subject to any disclaimer, the term of this patent is extended or adjusted under 35 U.S.C. 154(b) by 0 days.

(21) Appl. No.: 13/102,670

(22) Filed: May 6, 2011

(65) Prior Publication Data
US 2011/0217283 A1    Sep. 8, 2011

Related U.S. Application Data

(63) Continuation of application No. 12/327,345, filed on Dec. 3, 2008, now abandoned, which is a continuation of application No. 10/491,675, filed as application No. PCT/EP02/11093 on Oct. 2, 2002, now abandoned.

(30) Foreign Application Priority Data

Oct. 5, 2001 (DE) .................. 101 49 030

(51) Int. Cl.
C12P 21/06 (2006.01)
A61K 9/19 (2006.01)
(52) U.S. Cl. ...................... 435/69.1; 424/1.11
(58) Field of Classification Search ............. 514/12
See application file for complete search history.

(56) References Cited

U.S. PATENT DOCUMENTS

| 3,932,943 | A | * | 1/1976 | Briggs et al. ............ 34/287 |
| 5,710,257 | A | | 1/1998 | Seilhamer et al. |
| 6,238,664 | B1 | | 5/2001 | Hellerbrand et al. |
| 6,271,368 | B1 | * | 8/2001 | Lentzen et al. ......... 536/23.6 |
| 2002/0045208 | A1 | * | 4/2002 | Eck et al. .............. 435/69.1 |

FOREIGN PATENT DOCUMENTS

| DE | 4221836 | | 1/1994 |
| EP | 0306824 | | 3/1989 |
| EP | 0430200 | | 6/1991 |
| EP | 0602686 | | 6/1994 |
| EP | 0751221 | | 1/1997 |
| EP | 19716154 | | 10/1998 |
| WO | WO 97/01636 | * | 1/1997 |

OTHER PUBLICATIONS

Carpenter et al., "Rational Design of Stable Lyophilized Protein Formulations: Some Practical Advice", Pharmaceutical Research, 1997, 14(8), 969-975.*
Allison et al., "Hydrogen bonding between sugar and protein is responsible for inhibition of dehydration-induced protein unfolding," Archives of Biochemistry and Biophysics 365(2):289-298 (1999).
Allison et al., "Optimization of storage stability of lyophilized actin using combinations of disaccharides and dextran," Journal of Pharmaceutical Sciences 89(2): 199-214 (2000).
Beuth et al., "Behavior of lymphocyte subsets and expression of activation markers in response to immunotherapy with galactoside-specific lectin from mistletoe in breast cancer patients," Clin. Investig. 70:658-661 (1991).
Beuth et al., "Influence of treatment with the immunomodulatory effective dose of the β-galactoside-specific lectin from mistletoe on tumor colonization in BALB/c-mice for two experimental model systems," In vivo 5:29-32 (1991).
Beuth et al., "Vergleichende Untersuchungen zur immunaktiven wirkung von galaktosid-spezifischem mistellektin," Arzneim.-Forsch./Drug Res. 43(1), 166-169 (1993).
Bocci, "Mistletoe (*Viscum album*) lectins as cytokine inducers and immunoadjuvant in tumor therapy. A review," Journal of Biological Regulators and Homeostatic Agents 7(1):1-6 (1993).
Carpenter et al., "Freezing- and drying-induced perturbations of protein structure and mechanisms of protein protection by stabilizing additives," Pertubations of Protein Structure pp. 123-159 (1999).
Carpenter et al., "Separation of freezing- and drying-induced denaturation of lyophilized proteins using stress-specific stabilization," Archives of biochemistry and biophysics 303(2):456-464 (1993).
Dulat et al., "Down-regulation of human alloimmune responses by genetically engineered expression of CD95 ligand on stimulatory and target cells," Eur. J. Immunol. 31:2217-2226 (2001).
Endo et al., "The mechanism of action of the cytotoxic lectin from *Phoradendron californicum*: the RNA n-glycosidase activity of the protein," Febs Letters 248(1,2):115-118 (1989).
Endo et al., "The site of action of six different ribosome-inactivating proteins forom plants on eukaryotic ribosomes: the RNA n-glycosidase activity of the proteins," Biochemical and Biophysical Research Communications 150(3):1032-1036 (1988).
Everse et al., "Lyophilization Methods in Enzymology", vol. 22, pp. 33-39 (1971).
Estimated pl of SEQ ID No. 2 from Eck et al., 2002/0045208 (no date).
Franz et al., "Iolierung and charakterisierung von inhaltsstoffen der mistel (*Viscum album* I.)," Acta Biol. Med. Germ., 36:113-117 (1977).
Gabius et al., "Die Misteltherapie auf dem naturwissenschaftlichen prüfstand," Hahrgang 22(139):9-14 (1994).
Gabius et al., "From ill-defined extracrts to the immunomodulatory lectin: will there be a reason for oncological application of mistletoe?," Planta Med. 60:2-7 (1994).
Gabius et al., "The immunomodulatory β-galactoside-specific lectin from misteltoe: partial sequence analysis, cell and tissue binding, and impact on intracellular biosignaling of monocytic leukemia cells," Anticancer Research 12:669-676 (1992).
Ganguly et al., "Plant lectins as inhibitors of tumour growth and modulators of host immune response," Chemotherapy 40:272-278 (1994).

(Continued)

*Primary Examiner* — Suzanne M Noakes
(74) *Attorney, Agent, or Firm* — Novak Druce Connolly Bove + Quigg

(57) ABSTRACT

The invention relates to a method for the production of a medicament containing a polypeptide comprising at least one recombinant carbohydrate-binding polypeptide, or a functional fragment or derivative of said carbohydrate-binding polypeptide in a form stable for storage. The polypeptide mentioned comprises polypeptides or functional derivatives thereof, which are fused with cytotoxically effective peptides to give fusion proteins, or which are linked to another polypeptide having a cytotoxic activity. Moreover, the invention describes further formulating of the disclosed medicaments to medicaments with different pharmaceutical forms.

31 Claims, 11 Drawing Sheets

OTHER PUBLICATIONS

Figure 1:
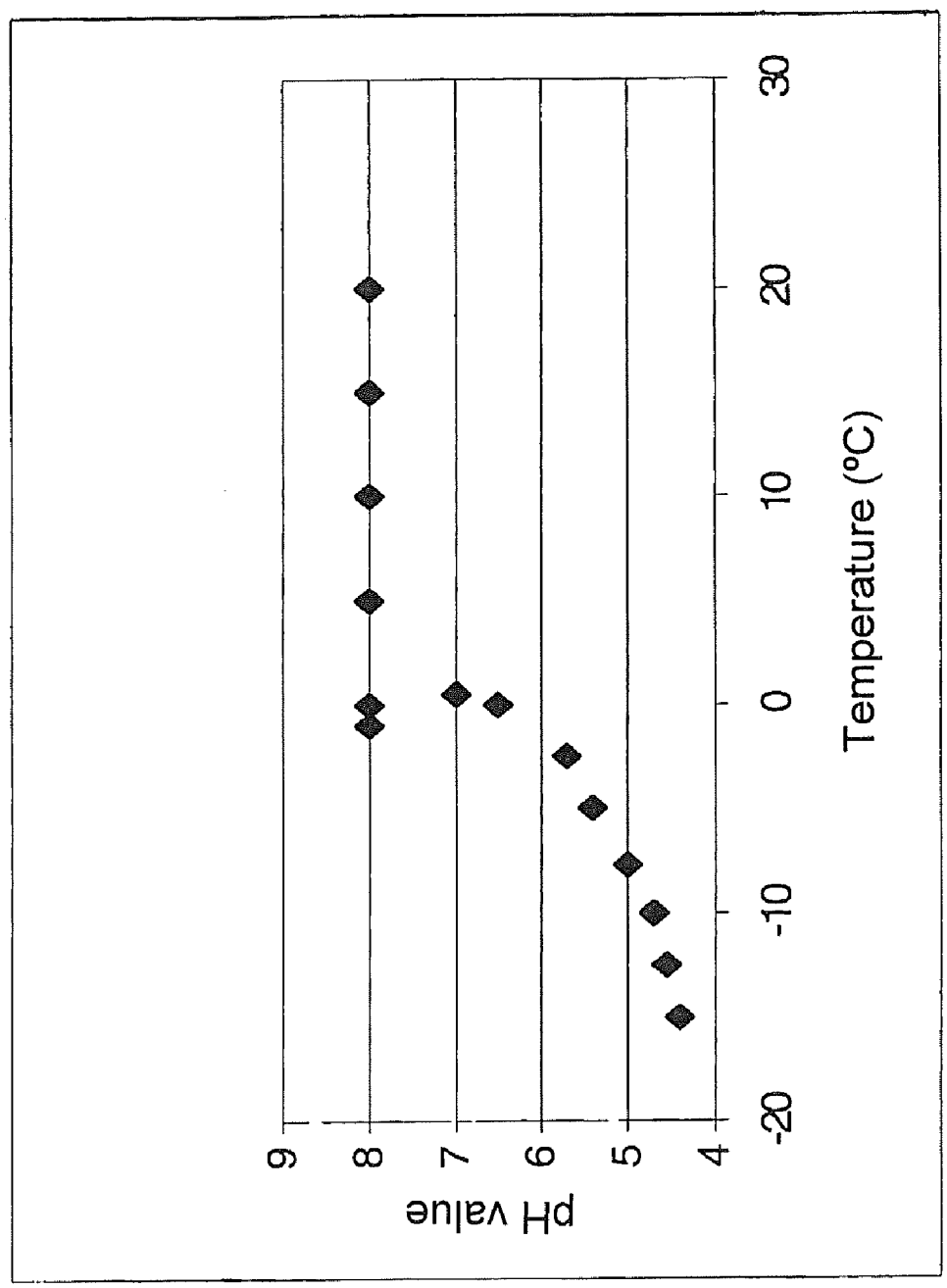

Gloger et al., "Influence of Freezing on the pH-shift of Different Buffer Systems", in Proceedings of the 3rd World Meeting of Pharmaceutics, Biopharmaceutics and Pharmaceutical Technology, R. Mueller (Ed.) APV/APGI, Mainz, Germany (2000), pp. 967-968.

G. Glinsky, "Anti-adhesion cancer therapy", Cancer and Metastasis Reviews 17:177-185 (1998).

E. Gorelik et al., "On the role of cell surface carbohydrates and their binding proteins (lectins) in tumor metastasis", Cancer and Metastasis Reviews 20:245-277 (2001).

Hajto et al., "Increased secretion of tumor necrosis factor a, interleukin 1, and interleukin 6 by human mononuclear cells exposed to β-galactoside-specific lectin from clinically applied mistletoe extract," Cancer Research 50:3322-3326 (1999).

Hajto et al., "Modulatory potency of the β-galactoside-specific lectin from mistletoe extract (iscador) on the host defense system in vivo in rabbits and patients," Cancer Research 49:4803-4808 (1989).

Hajto, "Immunomodulatory effects of iscador: a *Viscum album* preparation," Oncology 43(1):51-65 (1986).

Heiny et al., "Mistletoe extract standardized for the galactoside-specific lectin (ML-1) induces β-endorphin release and immunopotentiation in breast cancer patients," Anticancer Research 14:1339-1342 (1994).

Kaltner et al., "Animal Lectins: From Initial Description to Elaborated Structural and Functional Classification", The Molecular Immunology of Complex Carbohydrates-2, pp. 79-94 (2001).

Matzinger, "The JAM test—a simple assay for DNA fragmentation and cell death," Journal of Immunological Methods 145:185-192 (1991).

Männel et al., "Induction of tumor necrosis factor expression by a lectin from *Viscum album*," Cancer Immunolo. Immunother. 33:177-182 (1991).

Peumans et al., "Ribosome-inactivating proteins from plants: more than RNA N-glycosidases?," The FASEB Journal 1493-1506 (2001).

A. Raz et al., "Endogenous galactoside-binding lectins: a new class of functional tumor cell surface molecules related to metastasis", Cancer and Metastasis Reviews 6: 433-452 (1987).

H. Rudiger et al., "Plant lectins: Occurrence, biochemistry, functions and applications", Glycoconjugate Journal 18, 589-613 (2001).

\* cited by examiner

STABLE GALENIC FREEZE-DRIED PHARMACEUTICAL PREPARATION OF RECOMBINANT CARBOHYDRATE-BINDING POLYPEPTIDES

REFERENCE TO RELATED APPLICATIONS

This application is a continuation of application Ser. No. 12/327,345, filed Dec. 3, 2008, which is a continuation of application Ser. No. 10/491,675, filed Apr. 2, 2004, which is a national stage filing under 35 U.S.C. 371 of PCT application PCT/EP02/11093, filed Oct. 2, 2002, which claims the benefit of priority from German Application No. 101 49 030.5, filed Oct. 5, 2001, the specifications of each of which are incorporated by reference herein in their entirety. PCT Application PCT/EP02/11093 was published under PCT Article 21(2) in German.

FIELD OF THE INVENTION

The invention relates to a method for the production of a medicament containing a polypeptide, comprising at least one recombinant carbohydrate-binding polypeptide or a functional fragment or derivative of said carbohydrate-binding polypeptide in a form stable for storage. Said polypeptide comprises polypeptides or functional derivatives thereof fused to cytotoxically effective peptides to give fusion proteins or which are connected to a further polypeptide having cytotoxic activity. The invention further relates to the further formulation of the disclosed medicaments to give medicaments of various dosage forms.

BACKGROUND OF THE INVENTION

In recent years, medicinal research has uncovered a broad spectrum of diseases that can be treated with recombinant proteins. Examples of proteins of human origin are insulin, EPO and G-CSF the dosage forms and kinds of application of which have been described in various European patents. EP 0 430 200 B1 describes the application of human proteins for subcutaneous and intramuscular administration. Medicaments with stabilised human proteins which contain, amongst others, urea or different amino acids, are known from EP 0 306 824 B1. In this patent, EPO and G-CSF are given as examples. EP 0 607 156 B1 describes the production of conserved medicaments with human proteins for infusion or injection purposes.

In general, the term "recombinant" refers to proteins which are prepared using the recombinant DNA technique. These methods comprise cloning of the gene encoding the protein in question, inserting corresponding cDNA or genomic DNA in a suitable vector system and transforming/transfecting said vectors in suitable host organisms (bacteria or eukaryotic cells). If the cloned gene is expressed in the host organism, the corresponding protein can be recovered from the culture supernatant (if the protein expressed is secreted) or from a homogenate of the host organism (if the corresponding protein is expressed in an intracellular manner). Methods for producing recombinant proteins have been described for both animal and plant proteins. An example of the exact procedure for producing a dimeric plant protein is described in EP 0 751 221B1. This patent describes, amongst others, the unprecedented successful cloning of the genes encoding the ML-subunits. Furthermore, in this patent, the use of said dimeric plant proteins produced recombinantly for the preparation of medicaments is described, too.

The use of mistletoe extracts (extracts of Viscum album) as a curative has been known for centuries. Active ingredients called lectins have been identified as effective components of these extracts. These lectins are proteins which recognise very specific carbohydrate structures also in lipid- or protein-bound form and which bind thereto. Mistletoe lectin which has been characterised as ribosome-inactivating class II protein is pharmacologically effective by the interplay of its two subunits. The B-chain of the mistletoe lectin which has sequence motifs with specific carbohydrate binding properties is, in this case, responsible for the transport of the protein to the target cell. In the target cell, the A-subunit then blocks the ribosomal metabolism of the cell due to its enzymatic rRNA-N-glycosidase activity and, in this way, it triggers a programmed cell death (apoptosis) in said cell.

The pharmaceutical preparations which have so far been known from the state of the art generally contain human proteins, humanised proteins, extracts containing plant proteins or proteins isolated from plants. It is decisive for the effectiveness of preparations containing proteins that the biological activity of said proteins is maintained. For rViscumin, it is, for example, the dimeric structure and the activities that are to be attributed to the single chains and the specific pharmacological mode of action of said molecules that are to be maintained. Maintaining these biological activities strongly depends on the pH of the solution containing the proteins (cf. FIG. 1). Furthermore, storage conditions of the preparation in question influence the stability of a drug/medicament.

The mode of action of the mistletoe plant and the extracts obtained therefrom for treating diseases has been described in European patent EP 0 602 686 B1. As explained in this specification, mistletoe extracts have been used for therapeutic purposes for centuries. Since the beginning of this century, mistletoe preparations are used in cancer therapy with varying success (Bocci, 1993; Gabius et al., Gabius & Gabius, 1994; Ganguly & Das, 1994). Hajto et al. (1989, 1990) were able to show that the therapeutic effects are mediated in particular by so-called mistletoe lectins (viscumins, Viscum album agglutinins, VAA). Apart from a cytotoxic effect, nowadays, in particular an (unspecific) immunostimulation is discussed, the positive effects of which are utilised for an accompanying therapy and for aftercare of tumour patients. An increase in the life quality of such patients is possibly mediated by the release of enogenous endorphins (Heiny and Beuth, 1994).

Numerous tests in vitro (Hajto et al., 1990; Mannel et al., 1991; Beuth et al., 1993a) and in vivo (Hajto, 1986; Hajto et al., 1989; Beuth et al., 1991; Beuth et al., 1992), as well as clinical studies (Beuth et al., 1992) prove the increased release of inflammatory cytokines (TNF-$\alpha$, IL-1, IL-6) mediated by mistletoe lectin as well as an activation of cellular components of the immune system (TH cells, NK cells).

Today a 60 kDa mistletoe lectin protein is considered an active principle of the mistletoe extracts, wherein the mistletoe lectin can be recovered from extracts in a biochemical manner (Franz et al., 1977; Gabius et al., 1992). The ML protein consists of two covalently S—S-coupled subunits, the A-chain of which is responsible for an enzymatic inactivation of ribosomes (Endo et al., 1988) and the B-chain of which is responsible for the carbohydrate binding. The biological activity is correlated with obtaining the lectin activity of the B-chain (Hajto et al., 1990).

SUMMARY OF THE INVENTION

The use of a form of the medicament or a pharmaceutical preparation with rViscumin as an active component is an interesting an advantageous alternative for a plant preparation as it is now possible to use a chemically classified substance as a medicament. It is with regard to the high toxicity of the mistletoe lectin that the use of recombinantly produced proteins makes a good tolerance possible thanks to exact dosage. In this case, a form of the medicament or a pharmaceutical preparation is of particular advantage which is storage-stable over a long period of time, i.e. several months and preferably at least one year. Storage of the form of the medicament or the pharmaceutical preparation in said storage-stable form should moreover be simple and should be possible without sophisticated technology. Furthermore, it should be possible to simply further formulate the form of the medicament or the pharmaceutical preparation to a corresponding dosage form if its storage-stable form is not the same as its dosage form. With aqueous formulations according to the state of the art, storage periods of less than 10 weeks (2.5 months) are realistic under storage conditions of 2-8° C. (fridge).

Therefore, the technical problem underlying the present invention was to provide a method for producing a medicament or pharmaceutical preparation in a stable form for long-term storage which guarantees simple use both with regard to storage and administration and, optionally, its preparation. In this case, the medicament of the invention is to comprise at least one recombinant carbohydrate-binding polypeptide or a functional fragment or derivative of said polypeptide, furthermore, optionally, containing a pharmacologically acceptable carrier.

This technical problem is solved by the embodiments characterised in the claims.

As a consequence, the present invention relates to a method for producing a medicament containing a polypeptide comprising at least one recombinant carbohydrate-binding polypeptide or functional fragment or derivative of said polypeptide in a form stable for long-time storage, moreover, optionally, containing a pharmaceutically acceptable carrier comprising the step of cooling, freezing, spray drying or lyophilising while retaining the pharmacological properties of the polypeptide in the solution, wherein the solution is characterised in that the pH value of the solution is higher than pH 6.0 and a buffer system contained in the solvent guarantees that this pH-value is maintained.

DETAILED DESCRIPTION OF THE INVENTION

Starting from the corresponding cloned genes, recombinant polypeptides and proteins can be presented using conventional methods of molecular biology. Amongst others, these have been described in the textbook "Gentechnologie" (Old and Primrose, 1992) or in the laboratory manuals "Methods for General and Molecular Bacteriology" (Gerhardt et al., Chapter 18) or "Molecular Cloning: A Laboratory Manual" (Sambrook et al. 1993).

In accordance with the invention, a "carbohydrate-binding polypeptide" is a polypeptide which has the property that it specifically binds to certain carbohydrates. Examples of such carbohydrates are galactose, N-acetyl-galactosamine, modified galactose, neuraminic acids, low-molecular saccharides and oligosaccharides with terminal galactose and/or terminal galactosamine moieties or modified galactose moieties or terminal neuraminic acid moieties, and peptides and lipids having a corresponding carbohydrate function. "Functional fragments or derivatives of said polypeptide" of the invention are characterised in that they also have a specificity for binding to the above-mentioned carbohydrates.

The use of the polypeptides of the invention, such as e.g. rVisumin and other plant, dimeric class II polypeptides of ribosome-inactivating proteins (RIP II) for producing highly effective medicaments has been described amongst others in EP 0 751 221B 1. However, said medicaments are preferred to be administered one year after preparation at most.

Within the meaning of the invention, a medicament or pharmaceutical preparation is considered storage-stable if it can be stored over a long period of time, i.e. several months, that is more than six months, without a significant change of the specific properties of the pharmaceutical preparation and the polypeptide and, therefore, the effectiveness of said medicament or preparation being observed. In this context, a storage-stable form of the medicaments or pharmaceutical preparations according to the invention, which are stored over a period for 1, 2, 3, 4 or 5 years, is preferred. Preferably they can be stored under storage conditions that are common in the market and to be adhered to by distributors and applicants (2-8° C. and/or ambient temperature below 25° C.) without a significant change in the specific properties of the pharmaceutical preparation and the polypeptide and, therefore, the effectiveness of said medicament or preparation being observed. Thus, the invention relates to storage and transport forms of the polypeptides described herein, which are very well manageable.

The formulation of the medicament of the invention is optionally effected in combination with a "pharmacologically acceptable carrier" and/or diluent. Examples of particularly suitable pharmacologically acceptable carriers are known to those skilled in the art and comprise buffered saline solutions, water, emulsions such as e.g. oil/water emulsions, various kinds of detergents, sterile solutions, etc. Medicaments that comprise such carriers can be formulated using known conventional techniques. These medicaments can be administered to an individual in a suitable dose. Administration can be effected orally or parentally, e.g. intravenously, intraperitoneally, subcutaneously, intramuscularly, locally, intranasally, intrabronchially or intradermally or via a catheter at a site in an artery. The kind of dosage is determined by the attending physician in accordance with the clinical factors. The person skilled in the art knows that the kind of dosage depends on various factors such as, e.g. the patient's height or weight, body surface, age, sex or general health, but also on the particular agent to be administered, the duration and kind of administration and on other medicaments which are possibly administered in parallel. A typical dose can, for instance, range from 0.001 to 1000 μg wherein doses below or above this exemplary range are thinkable, in particular when the aforementioned factors are taken into consideration. In general, if the composition of the invention is administered regularly, the dose should range from 10 ng to 10 mg units per day or per application interval. If the composition is to be administered intravenously, the dose should range from 1 ng and 0.1 mg units per kilogram body weight per minute.

The composition of the invention can be administered locally or systemically. Preparations for parenteral administration comprise sterile aqueous or non-aqueous solutions, suspensions and emulsions. Examples of non-aqueous solvents are propylene glycol, polyethylene glycol, plant oils such as, e.g. olive oil, and organic ester compounds such as, e.g. ethyloleate, which are suitable for injections. Aqueous carriers include water, alcoholic-aqueous solutions, emulsions, suspensions, salt solutions and buffered media. Parenteral carriers comprise sodium chloride solutions, Ringer's dextrose, dextrose and sodium chloride, Ringer's lactate and bound oils. Intravenous carriers comprise, e.g. fluid supplements, nutrient supplements and electrolyte supplements (such as, e.g. those based on Ringer's dextrose). Furthermore, the composition of the invention can comprise preservatives and other additives such as, e.g. anti-microbial compounds, antioxidants, complex-forming agents and inert gasses. Furthermore, depending on the intended use, compounds such as, e.g. interleukins, growth factors, differentiation factors, interferons, chemotactic proteins or an unspecific immunomodulary agent.

The buffer substances used are suitable to maintain the adjusted pH within the ranges described during the phase of cooling, freezing, spray drying or lyophilising. The buffer substances are preferred to be selected in such a way that, with a low buffer capacity, it is not possible for the pH to change to lower values during freezing. By maintaining a high pH range during lyophilisation, the stability of the polypeptide is guaranteed. A low buffer capacity is moreover preferred for an injection solution ready for application. In Example 1, a method for checking the pH during cooling or freezing of pharmaceutical preparations is described. By means of this or similar methods, buffer substances can be determined which are suitable for the method of the invention.

In the state of the art, a plurality of medicaments are described which contain low-molecular, oligomeric compounds (including peptides) and high-molecular compounds (including polypeptides) in buffered solutions. In addition, for a plurality of such medicaments which contain corresponding compounds that are stable in a wide pH range methods for improving the storage properties have been described and are known to the skilled person. Examples thereof are methods comprising freezing, spray drying or lyophilising of medicaments. Due to said pH-independent stability, it has so far not been described that a specific control of the pH during lyophilising or spray drying was necessary. Moreover, conventional lyophilisation devices for producing medicaments and pharmaceutical preparations have not been supplied with means for controlling the pH.

When such known methods were used, it was surprisingly found that the lectin properties of rViscumin and other plant dimeric class II polypeptides of ribosome-inactivating proteins (RIP II) can, under certain circumstances, be sensitive to the pH of the particular solvent used in said method. Strong fluctuations of this value and, in particular, a strongly acidic medium can lead to a certain loss in specific lectin properties. Accordingly, maintaining the pre-determined pH is a necessary feature of the method of the invention. For maintaining these specific properties, a pH control of the solution is necessary in all processing stages in order to guarantee the stability of the polypeptide. in Example 1, a method for checking the pH during cooling or freezing of pharmaceutical preparations has been described.

In a preferred embodiment, the method described comprises a polypeptide containing
(a) the recombinant carbohydrate-binding polypeptide or a functional fragment or derivative of this polypeptide which is fused to a cytotoxically effective peptide to form a fusion protein;
(b) the recombinant carbohydrate-binding polypeptide or a functional fragment or derivative of this polypeptide which is linked to another polypeptide which has an enzymatic rRNA-N-glycosidase activity;
(c) the recombinant carbohydrate-binding polypeptide or a functional fragment or derivative of this polypeptide which is linked to another polypeptide in which an enzymatic rRNA-N-glycosidase activity has been replaced by another cytotoxic activity; or
(d) the recombinant carbohydrate-binding polypeptide or a functional fragment or derivative of this polypeptide, which is linked to a fusion protein, comprising a polypeptide with an enzymatic rRNA-N-glycosidase activity and/or another cytotoxic activity.

In accordance with this preferred embodiment of the invention, the recombinant carbohydrate-binding polypeptide or a functional fragment or derivative of said polypeptide is bound to another peptide which has cytotoxic activity. Said binding of the peptides can be both a covalent binding and a binding based on other physico-chemical interactions. Examples of covalent binding of the peptides of the invention comprise both peptide bonds which are, amongst others, characteristic of fusion proteins and disulfide bonds.

Within the meaning of the invention, the carbohydrate-binding polypeptide or functional fragment or derivative of said polypeptide permits an interaction of the protein with the cell surface of the target cell. Subsequently, the peptide having cytotoxic activity acts either directly on the cell surface (e.g. by forming pores in the cell membrane) or after absorption into the cell (e.g. by inhibiting or destroying the protein biosynthesis, by inducing an apoptosis signal cascade or by inhibiting or destroying the activity of the mitochondria). The cytotoxic activity can be checked using various tests that are known to the skilled person ("JAM test", cf. Matzinger (1991), "$^{51}$Cr release test", "Propidium iodide staining of cells" or "Annexin V test", cf. Dulat (2001)).

Examples of peptides having enzymatic rRNA-N-glycosidase activity of ribosome-inactivating proteins (RIPS) are described, amongst others, by Endo et al. (1988 and 1989) and in an overview article by Peumans et al. (2001).

In another preferred embodiment of the method, the recombinant carbohydrate-binding polypeptide is the B-chain of a ribosome-inactivating protein.

In another embodiment which is preferred, too, the further polypeptide which is linked to the recombinant carbohydrate-binding polypeptide is the A-chain of a ribosome-inactivating protein.

In another embodiment which is furthermore preferred, the B-chain and/or A-chain of the ribosome-inactivating protein corresponds to the B-chain or A-chain of a ribosome-inactivating protein of the type II. Said ribosome-inactivating type II-protein is preferred to be rViscumin. Both the function and the recombinant presentation of the holoenzyme rViscumin as an example of a ribosome-inactivating protein have been described in EP 0 751 221B1.

In another preferred embodiment of the method, it is guaranteed that the pH of the solution is between 6.0 and 9.0, more preferably, the pH of the solution is between 7.5 and 8.5. As illustrated in the examples, a pH of 8.0 is particularly preferred. A less preferred pH range of the solution is the range above pH 12 as in such high pH ranges, a deamidation is to be expected and, as a consequence, the properties of the polypeptide as a medicinal active agent would change. Without excluding higher pH ranges, in the method of the invention, usually a pH of higher than 6.0 and lower than pH 12 is to be selected. However, the person of skill in the art can indeed also select pH ranges higher than pH 12. In this case, it is however preferred that the pH of the medicament is adjusted to a physiological pH range prior to administration to the patient. A method for controlling the pH while carrying out the method of the invention, is described in Example 1.

A method in which the salt or salts of the buffer system are used in a final concentration ranging from 0.6% to 2.4% (5 mM to 200 mM) is preferred, too. Furthermore, a method in which the salt or salts of the buffer system are used in a final concentration ranging from 100 mM to 200 mM is furthermore preferred. Accordingly, for instance, a final concentration for Tris base of 100 nM to 200 nM (1.2% to 2.4%) is preferred as in all studies carried out in connection with this invention using optimised formulations a loss in rViscumin of only 5% caused by the process was observed. For the final concentration ranging from 20 mM to 100 mM a corresponding loss in the range of 10 to 15% was detected. As shown in the Examples, for a final concentration below the optimum concentration of 20 mM, a corresponding loss in the range of 10 to 20% was detected.

In connection with this invention, the expression “final concentration” refers to a concentration of the solution in mass/volume (m/v) which the person of skill in the art adjusts before the cooling, freezing, spray drying or lyophilisation process.

Moreover, a method is preferred in which the salt or salts of the buffer system is/are selected from the group comprising: TRIS/HCl, TRICIN/HCl, HEPES/HCl, ammonium carbonate buffer, TRIS/glutamic acid and TRIS/aspartic acid. As is described amongst others in the attached examples, said buffer systems guarantee that a high pH is maintained during a freezing phase in the corresponding solutions for the selected combinations of initial substances. For this reason, the corresponding buffer systems play a crucial role with regard to the stability of the polypeptide.

In another preferred embodiment of the method of the invention, one or more surfactants are used for stabilising the pharmacological properties of the polypeptide of the solution. Said surfactants serve as wetting agents, thus reduce the surface tension of a solution and favour wetting of lyophilisation products with a reconstitution solution. In addition, these substances occupy so-called “hot spots” on the walls of the preparation vessels used and primary packing agents used to which, for instance, rViscumin can preferably be bound as a hydrophobic protein. In the absence of wetting agents, loss in protein or protein activity during the production and packaging process and in the pharmaceutical solutions is likely. Moreover, the addition of wetting agents is advantageous to avoid loss after reconstitution of the lyophilised powder. Such loss would lead to an inaccurate dosage.

Non-ionic tensides are preferred to be used as surfactants, these being used in a final concentration ranging from 0.01 to 5.0%.

Preferred non-ionic tensides are selected from the group comprising: fatty alcohols, partial glycerides, polysorbates, polyoxyethylene fatty acid ethers and polyoxyethylene fatty acid esters, poloxameres (polyoxypropylene-polyoxyethylene-block polymers), saccharide fatty acid esters, polyoxyethylene sorbitol ethers and polyoxyethylene fatty acid ethers, polyoxy fatty acid esters and phosphatides.

Preferred examples of polysorbates are selected from the group comprising Polysorbate 80 and Polysorbate 20.

Moreover, preferred are polyoxyethylene fatty acid ethers and polyoxyethylene fatty acid esters Macrogol ethers or Macrogol esters, the poloxamer Pluronic F68, poloxamer 166 or 188 and the phosphatides such as, e.g. lecithins. In this connection, derivatives of lecithins from soy or chicken protein are also comprised.

Amphoteric tensides which are used in a final concentration ranging from 0.01 to 5.0% are also preferred as surfactants.

In another preferred embodiment of the method of the invention, for lyophilisation, one or more lyoprotectors in a final concentration ranging from 0.1 to 20% and/or cryoprotectors in a final concentration ranging from 0.01 to 1.0% are added to the solution. In this connection, lyoprotectors serve for the protection of the substances during drying, whereas cryoprotectors fulfil the corresponding task during freezing. The ranges of final concentration mentioned herein for use of lyoprotectors and/or cryoprotectors are deemed to be preferred, as a consequence, the method of the invention also comprises ranges of final concentration which are outside the preferred ranges of final concentration. The lyoprotectors are preferred to be used in a range of final concentration of 4.0 to 10%. In combination with the lyoprotectors or also in their absence, the cryoprotectors are preferred to be added to the solution at a final concentration ranging from 0.05 to 0.1%.

Furthermore, lyoprotectors are preferred which are selected from the group comprising:

a) low molecular saccharides such as glucose, trehalose and sucrose;

b) hexites such as mannitol (mannite) and sorbitol (sorbite);

c) oligomeric and polymeric saccharides such as cyclic beta-hydroxypropylcyclodextrin, cyclodextrins, cellulose, starch, carboxyamylopektin, chitosan and their derivatives;

d) anorganic gelling agents such as bentonites, and silicon dioxide; and e) synthetic polymers such as polyvinylpyrrolidones and polyacrylates.

Dextranes having a molecular mass of 1,000 to 100,000 Da and are preferred and more preferably 1,000 to 10,000 Da are used. As documented in the examples described herein, dextranes are preferred lyoprotectors which can preferably be used without mannitol, which can, however, indeed be used together with other lyoprotectors in the method of the invention. As shown in the examples, dextranes can preferably also be used alone (without other lyoprotectors) in the method of the invention. The fact that dextranes can be used alone as lyoprotectors in the method of the invention, in particular in the lyophilisation process, is surprising as it has been described in the state of the art that dextrane, as an accompanying adjuvant, can only contribute its share in stabilising proteins (Carpenter et al., 1993, Carpenter et al., 1999, Allison et al., 1999, Allison et al., 2000).

Ionic substances, too, are preferably used as cryoprotectors. These ionic substances are, in turn, preferably selected from the group consisting of sodium chloride, sodium sulphate, potassium chloride and potassium sulphate. According to the invention, sodium salts of edetic acid are also used. Said salts contribute to a further stabilisation of the polypeptides due to complex formation of metal cations taken up during the production process.

According to the method of the invention, lyoprotectors and cryoprotectors form amorphic structures during lyophilisation. These lyoprotectors and cryoprotectors prevent the formation of crystal grids (constant distances of atoms in a solid substance) during the lyophilisation process. The absence of crystalline structures in a solid substance can be detected by means of a powder crystalline structure analysis (e.g. by diffraction of x-rays).

In another preferred embodiment of the method, amino acids are used as stabilisers. Preferably, they are used in a concentration of 0.01 to 50 mg/ml. In addition to the stabilising property, amino acids themselves can be used as buffer substances according to the invention.

Furthermore, it is preferred that the amino acids are selected from the group comprising acidic amino acids such as glutamic acid and aspartic acid, the basic amino acid arginine and the neutral amino acid valine.

In another embodiment of the method of the invention, the polypeptide which comprises at least a recombinant carbohydrate-binding polypeptide or a functional derivative or a fragment of the recombinant carbohydrate-binding polypeptide is used in a final concentration of 0.000001% (10 ng/ml)

to 1.0% (10 mg/ml). In this case, a protein concentration of 0.00001% (100 ng/ml) 0.1% (1 mg/ml) is particularly preferred.

Another preferred embodiment of the method comprises the further formulation or reconstitution of the medicament as an aqueous or non-aqueous solution. Moreover, this includes the further formulation of the medicament as an injection, instillation or infusion solution. Depending on the ailments or diseases to be treated, injection solutions according to the invention are administered subcutaneously, intramuscularly, intravenously, intracardially or intraperitoneally. Solutions for installation into a body cavity are instilled, for example, into the urinary bladder, depending on the ailment to be treated.

In another preferred embodiment of the method, the further formulation or reconstitution of the medicament for gastrointestinal, oral, nasal, pulmonary, dermal, transdermal or local administration is also comprised.

Moreover, the further formulation of the medicament to give a juice, capsules, tablets, suppositories or gels is preferred, too.

The gels mentioned, which can be produced by further formulation of the medicament of the invention, can be obtained using inorganic and organic hydrogelling agents together with aqueous or aqueous/alcoholic solutions. In this case, gelling agents of natural, partially synthetic and synthetic origin are comprised. These molecules have an, in part, extreme swelling capability in common which leads to the formation of spreadable gels.

Moreover, the further formulation of the medicament to give a powder for inhalation which can be administered by use of an inhalator is also preferred.

The invention furthermore relates to a medicament which is prepared in accordance with one of the methods of the invention.

The invention also relates to the use of a polypeptide for producing such a medicament.

Depending on the further formulations, the administration of the medicament of the invention can be carried out in various ways, e.g. intravenously, intraperitoneally, subcutaneously, intramuscularly, locally or intradermally. The attending physician determines the kind of dosage in accordance with the clinical factors. The skilled person knows that the kind of dosage depends on various factors such as, e.g. the patient's height, body surface, age, sex or general health, but also on the special agent that is administered, the duration and kind of administration and other medicaments which are possibly administered in parallel.

The figures show

FIG. 1 In FIG. 1 the change in the pH value of a buffer solution dependent on the temperature is depicted. The buffer solution corresponds to a 20 mM phosphate buffer and moreover contains 0.1% sodium chloride. As described in example 1, this buffer solution was cooled down in a commercially available cryosate with temperature control. The pH value in the solution was determined with specially suitable pH electrodes. The cooling down rate in the depicted assay amounted to 1.2K. The course of the depicted curve shows that the cooling down of the buffer solution from room temperature to the freezing point of the solution had no significant effect on the pH value of this solution. If the solution is cooled down to temperatures below their freezing point, a marked decrease of the pH value of 8 to below 5 can be observed.

Figure 2:
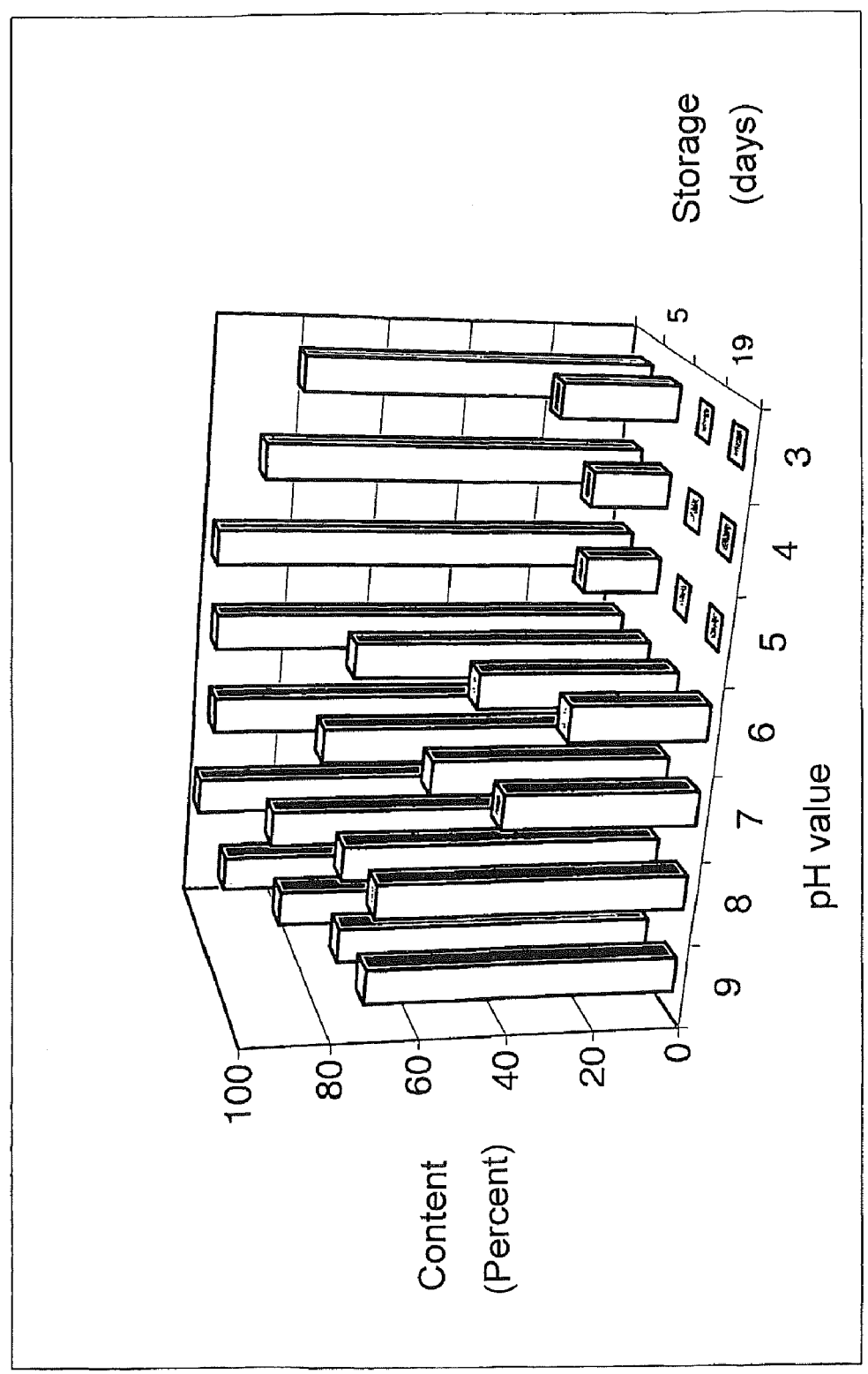

FIG. 2 In FIG. 2, the stability of carbohydrate-specific rViscumin dependent on the pH value and short-time storage at 2 to 8° C., rViscumin in buffered saline solution is shown. The buffer solution corresponds to a 20 mM phosphate buffer (ph 7.2) which was adjusted to pH values of 3, 4, 5, 7, 8 and 9 with NaOH (1M and 0.1M) or HCl (10% or 1%). Moreover, the phosphate-buffered solutions contain NaCl in a concentration of 0.7 to 0.9% for the adjustment of the isotonicity of the solutions and low-molecular polyvinylpyrrolidone in a concentration of 0.1 g/l for preventing an adsorption of the polypeptide to the surface of the vessel.

In the assay shown in the figure it was observed that the stability of the polypeptide rViscumin in the buffered solutions decreases markedly when the pH value decreases. Below a pH value of pH 6, no rVisumin with carbohydrate-specific properties is left after a short storage period only.

Figure 3:
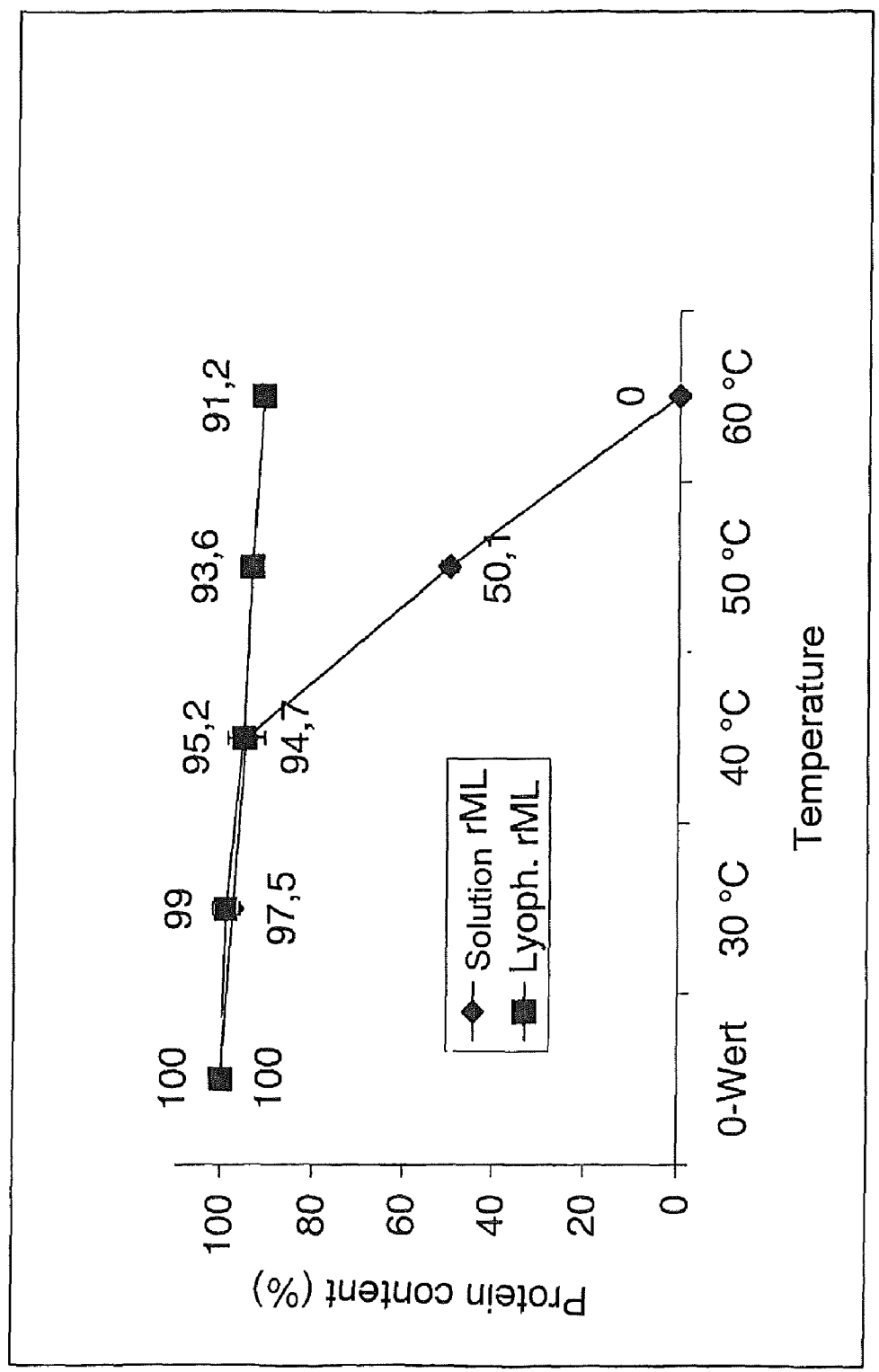

FIG. 3 FIG. 3 shows the stability of carbohydrate-specific rViscumin (rML) in a buffered stabilised solution and the lyophilised powder (lyophilisation product) produced therefrom, dependent on the temperature.

The buffer solution corresponds to a 200 mM Tris/HCl buffer (pH 8.0), containing 8.0% (w/v) dextrane T10, 0.1% (w/v) NaCl and 0.1% (w/v) Polysorbate 80. rViscumin is contained in the solution in a concentration of 2.0 µg/ml. The solution is distributed, treated and examined according to the assay described in example 3.

The result of the test shown in the figure shows that the content of rViscumin in the buffered, stabilised solution decreases markedly starting at a temperature of 40° C. At 50° C., only 50% of the initial concentration of rViscumin with carbohydrate-specific properties is detected. At 60° C., no carbohydrate-specific rViscumin is detected any more. Thus, the disintegration temperature of rViscumin in the solution lies between 40° C. and 50° C. The detected content of rViscumin with carbohydrate-specific properties in the solid only decreases very slowly as the temperature rises. At a temperature of 50° C. a content of 94% and at a temperature of 60° C. a content of 91% of the initial content can still be detected.

FIG. 4

Figure 4:
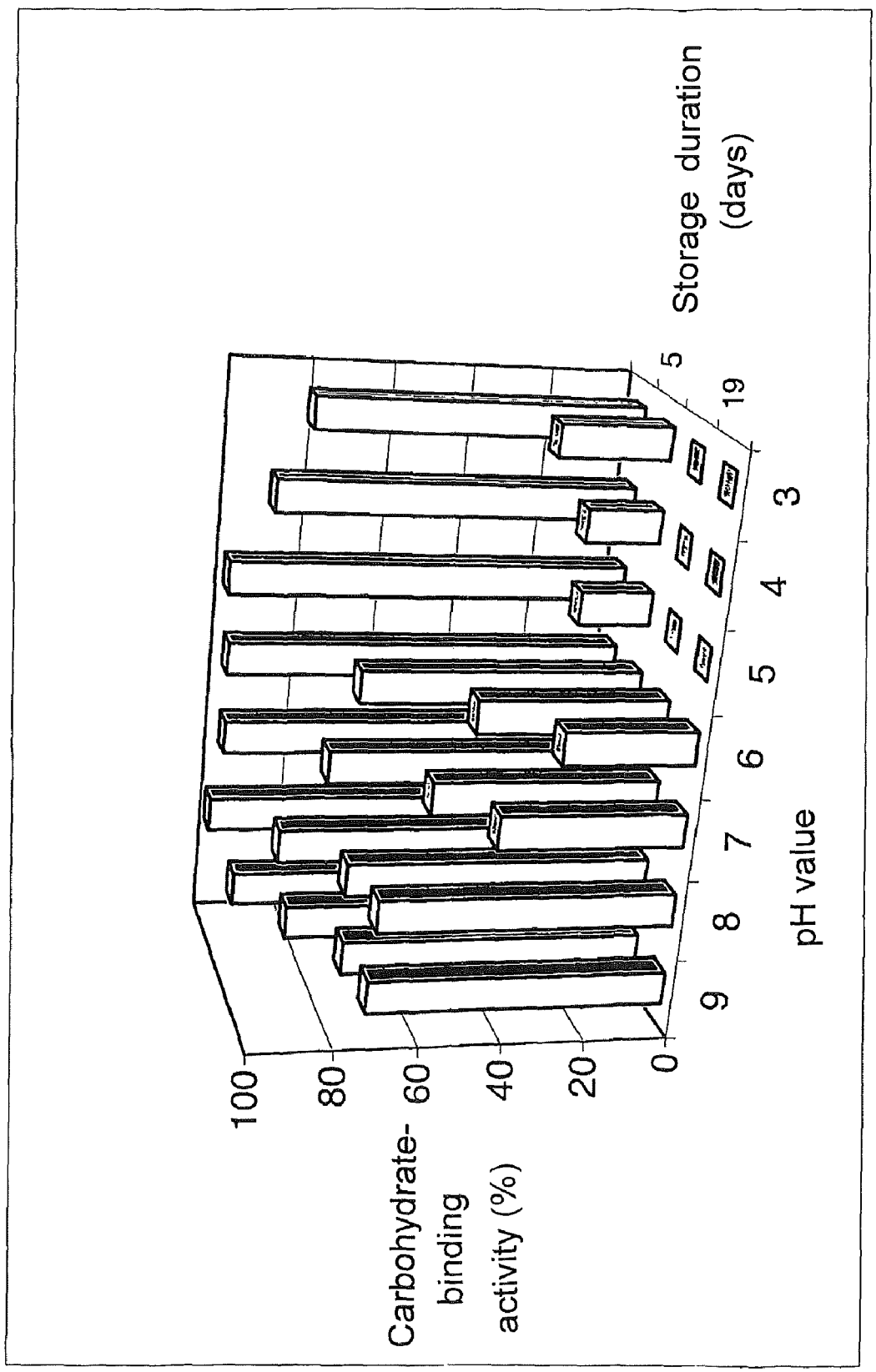

FIG. 4 exemplifies the dependence of the stability of the carbohydrate-binding activity of rViscumin in an aqueous solution when the pH value changes.

FIG. 5

Figure 5:
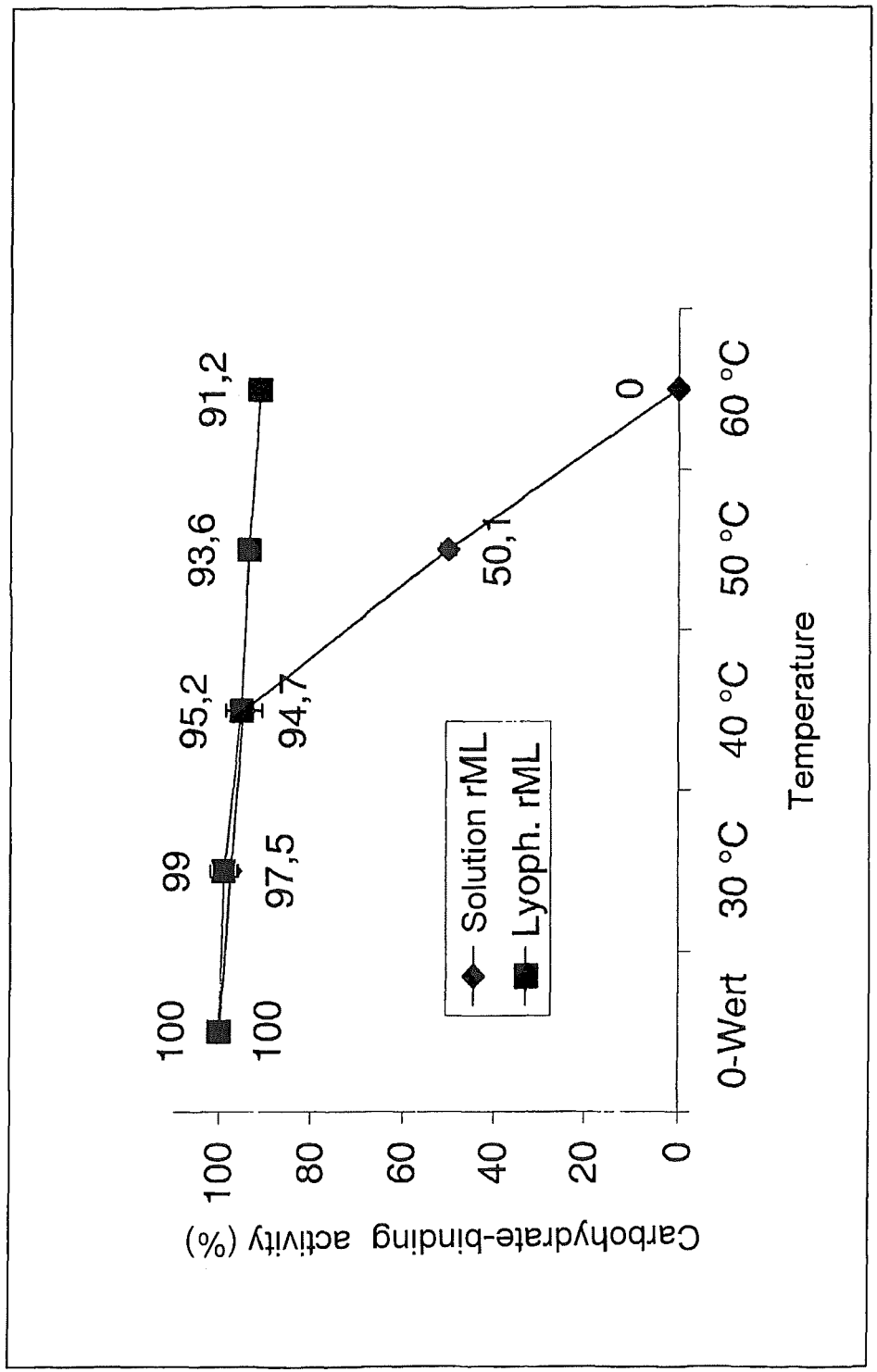

FIG. 5 shows the dependence of the carbohydrate-binding activity of rViscumin in an aqueous solution and as lyophilised powder with increasing temperature.

FIG. 6

Figure 6:
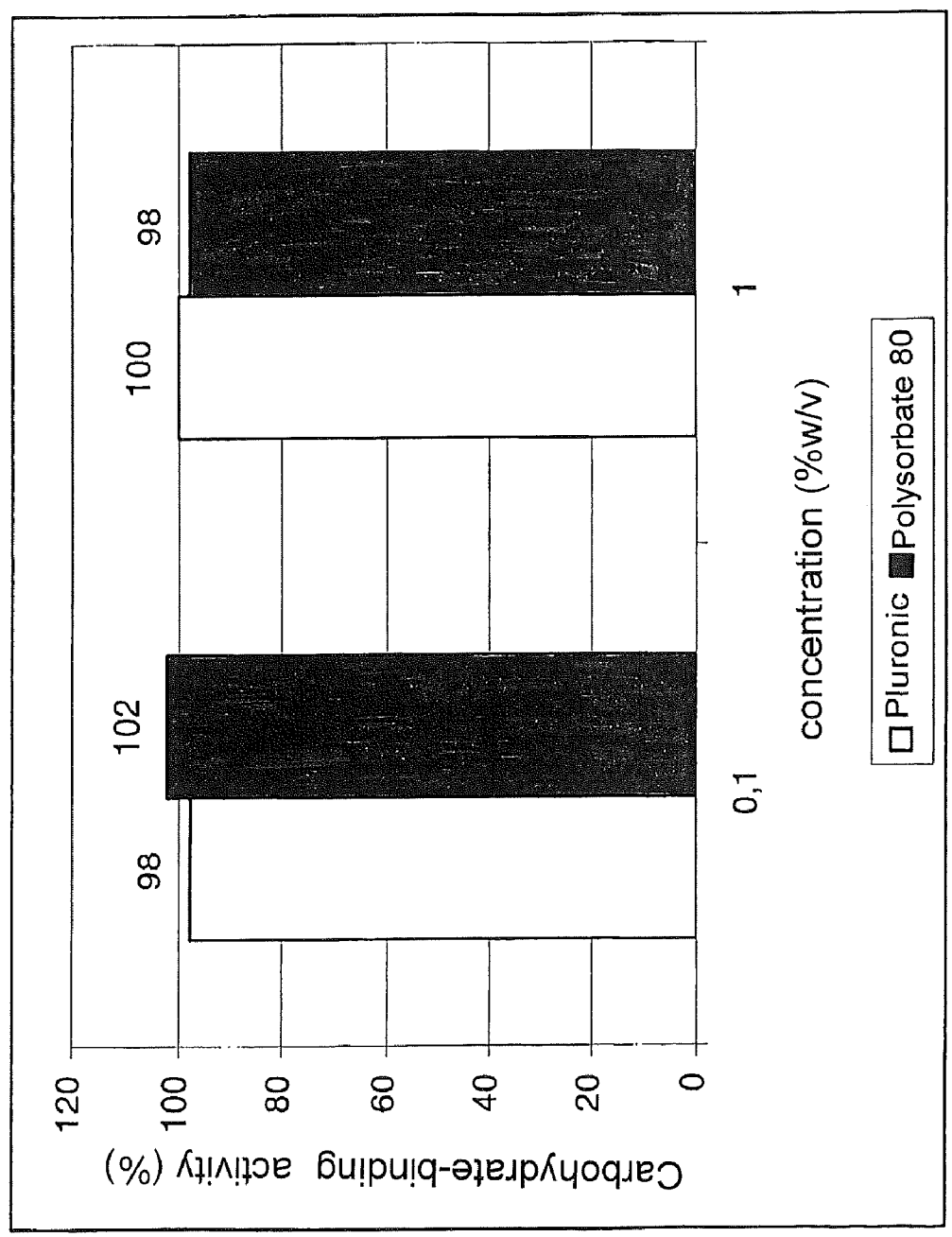

FIG. 6 shows the influence which the adjuvants Pluronic F68 and Polysorbate 80 in their role as cryoprotectors have on the process step freezing/thawing of an aqueous solution of rViscumin in 100 mM TRIS buffer pH 8.0. The solution contains the lyoprotector dextrane T1 in a concentration of 2% which is below the preferred range.

FIG. 7

Figure 7:
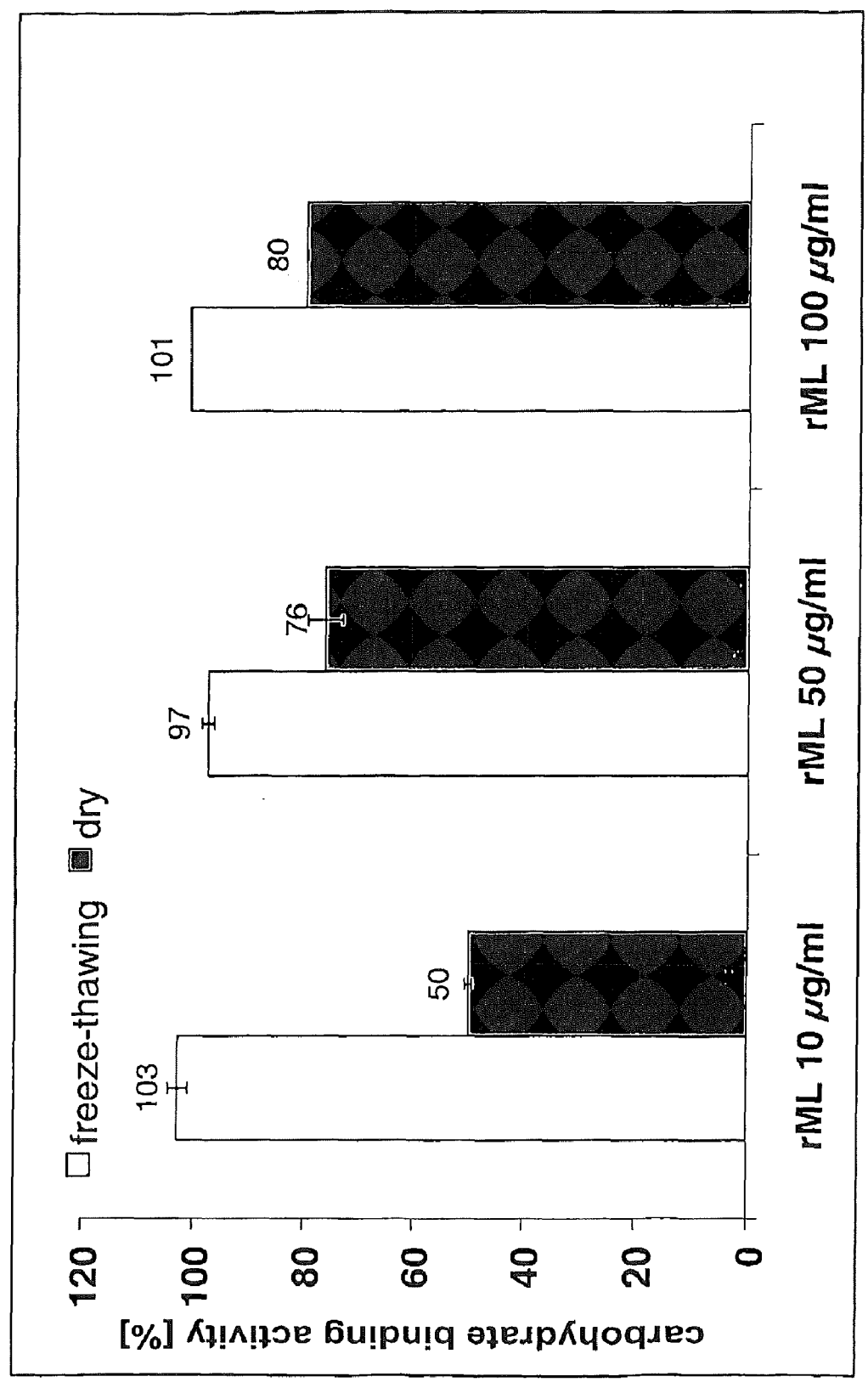

FIG. 7 shows the influence which the protein concentration of an aqueous solution of rViscumin has on the lyophilisation process.

FIG. 8

Figure 8:
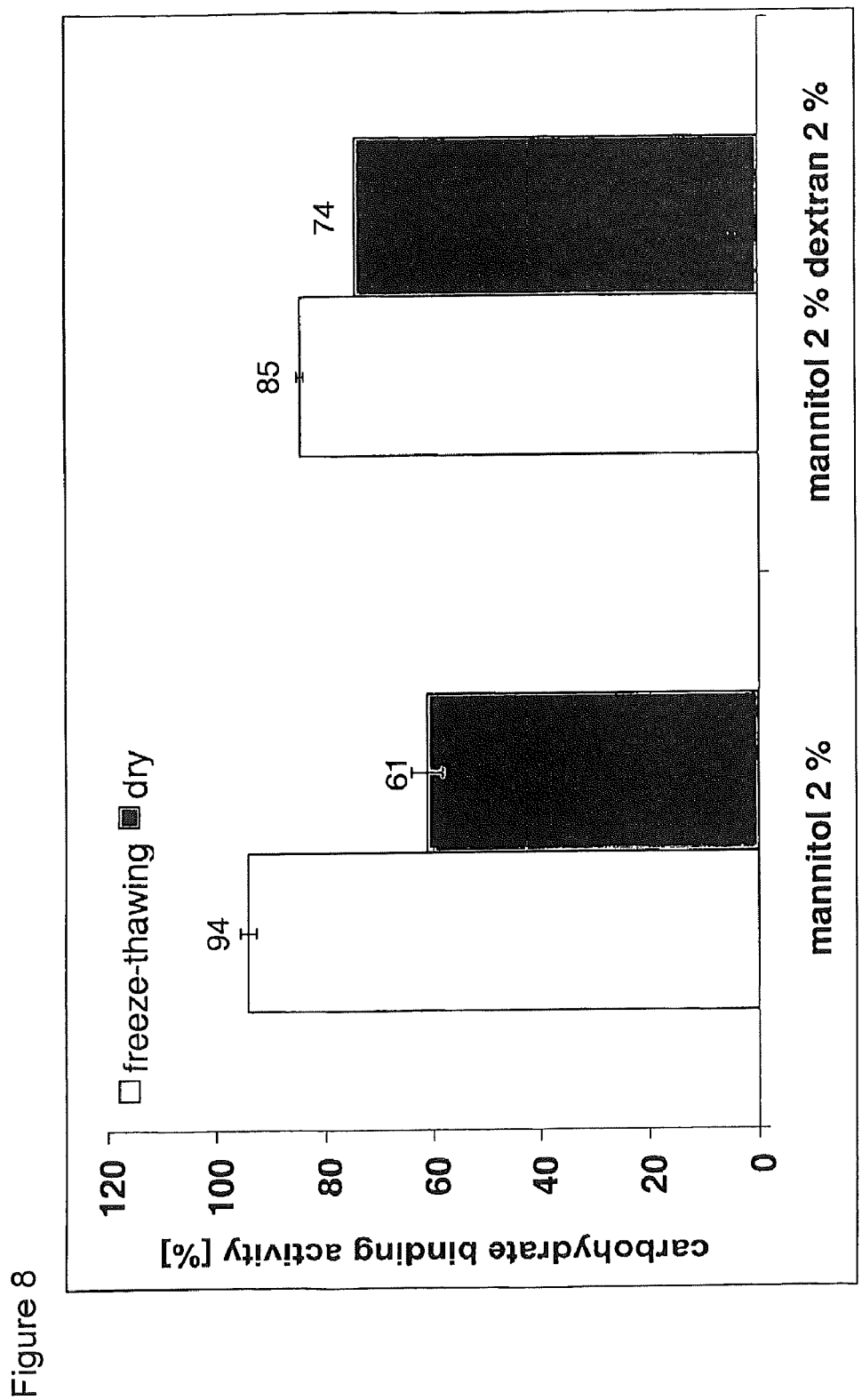

FIG. 8 shows the influence which the lyoprotector mannite and a mixture of mannite together with a non-crystallising kryoprotector has on rViscumin.

FIG. 9

Figure 9:
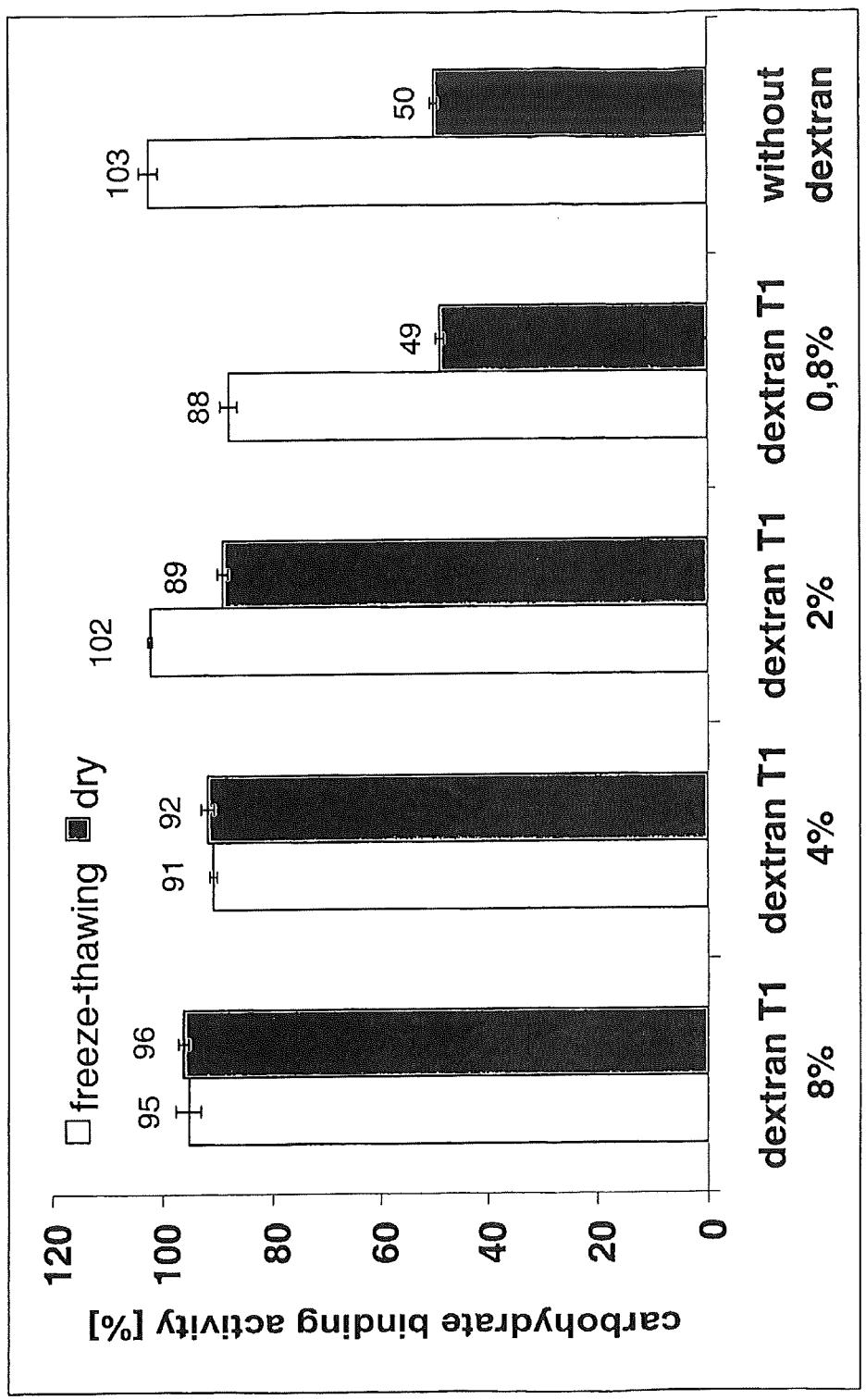

FIG. 9 shows the suitability and the optimal range of the cryoprotector dextrane T1 with regard to the stability of rViscumin during lyophilisation.

FIG. 10

Figure 10:
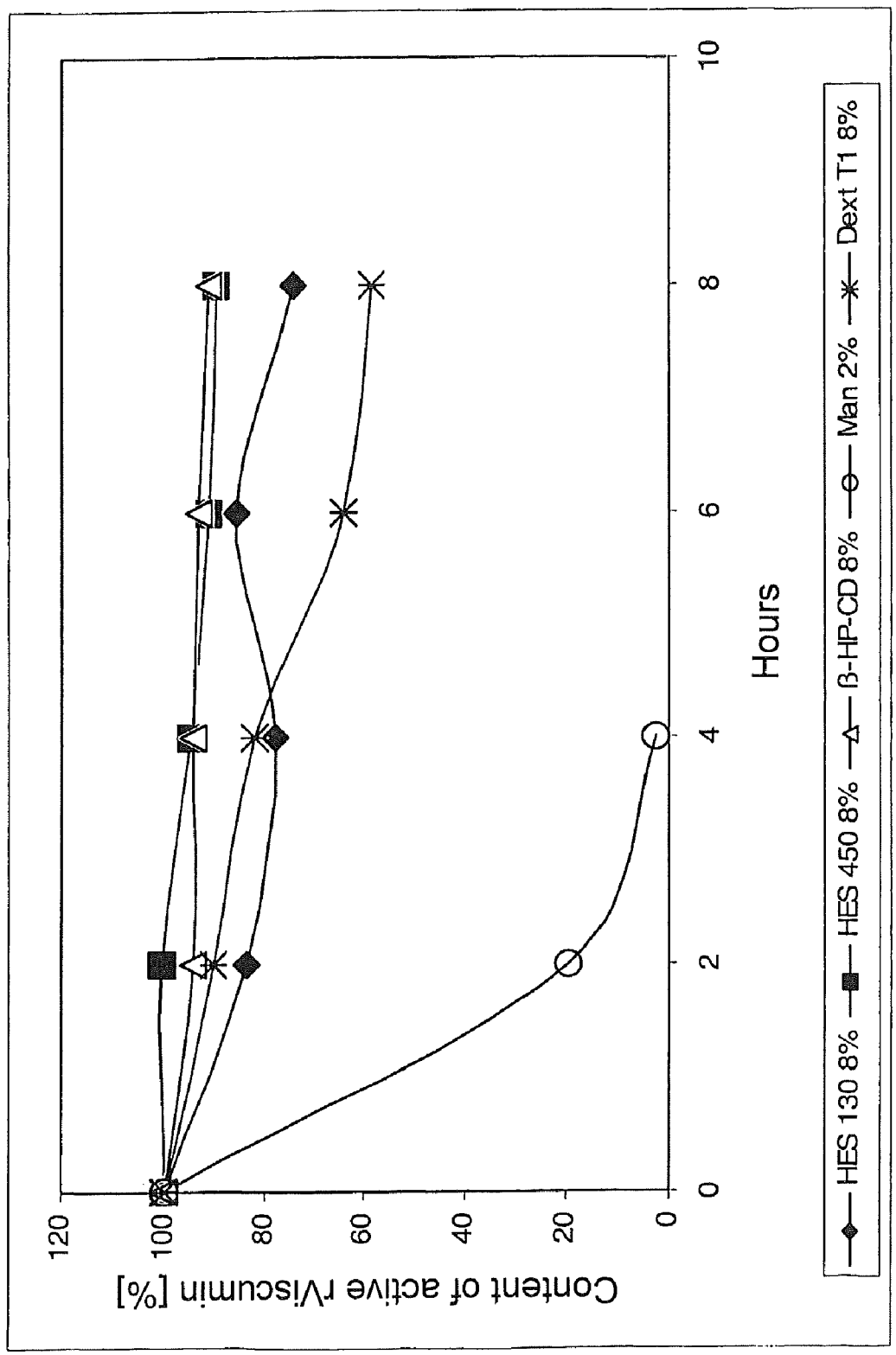

FIG. 10 shows the influence of different lyoprotectors on the stability of lyophilised rViscumin preparations at an increased temperature of 60° C.

FIG. 11

Figure 11:
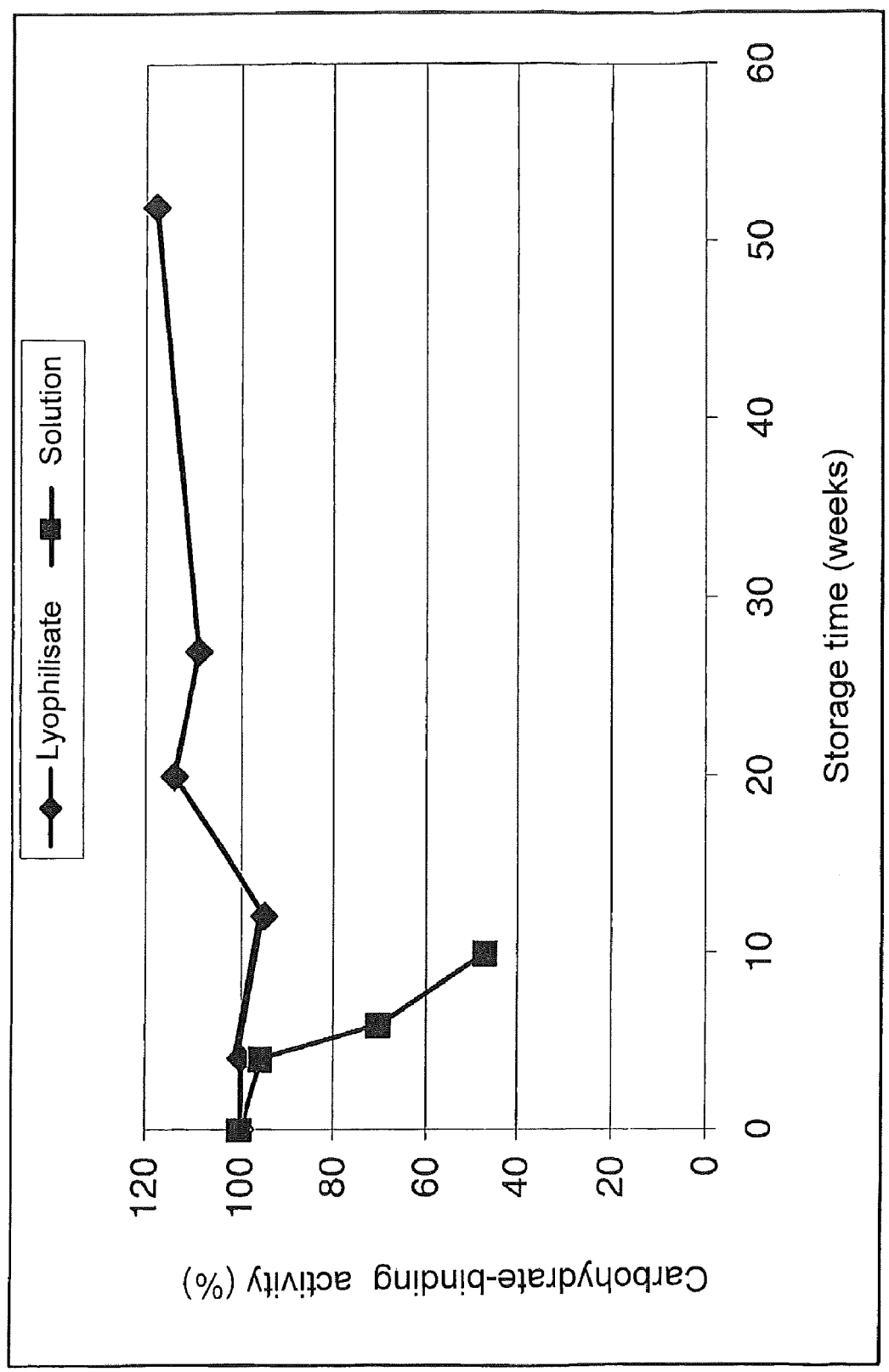

FIG. 11 shows the storage stability of an aqueous preparation of rViscumin (squares) over 10 weeks and of a lyophilised culture (rhombuses) over 56 weeks at a storage temperature of 2 to 8° C.

EXAMPLE 1

Method for Verifying the pH Value During the Cooling Down or the Freezing of Medicaments rViscumin is a dimeric recombinantly produced plant protein with sugar-specific binding activities. The pharmacological effect of the protein, triggering apoptosis in cells, correlates with obtaining the sugar-specific binding activity. Obtaining the sugar specificity largely depends on the pH value of the surrounding medium. If the pH value of the medium decreases, at a ph value of below 6.0, the sugar binding activity of rViscumin decreases markedly. This is also the case for pH changes during the freezing process of the lyophilisation of aqueous preparations with rViscumin. It is for this reason that the control of the pH of aqueous buffer systems during freezing of rVisumin pharmaceutical preparations in connection with lyophilisation is necessary.

The problem can be solved by producing pharmaceutical preparations of rViscumin or of its basic formulation without active agent (combination of buffer salts) in a volume of 15 ml in common freeze flasks (vials). The freeze flasks are placed into a commercially available cryostate with controlled temperature control. Special suitable pH electrodes (e.g. the pressure-resistant Sure-Flow pHuture Probe with Converter Model 605—power supply for ISFET electrodes, Orion or frost-resistant glass electrode, Schott Gerate GmbH, Hofheim) are used for pH determination. The registration of the pH values is carried out with commercially available pH-meters. A cooling down rate of 1.2K is suitable to picture the simulation of the cooling down rate of lyophilisers. The pH values in the solution are determined depending on the temperature.

FIG. 1 shows the temperature dependent course of the pH value of a 20 mM sodium phosphate buffer (ph 8.0 at room temperature).

With a decrease in temperature under 0° C., phosphate buffers show an erratic and strong decrease of the pH value as can be proved by the example of the 20 mM phosphate buffer with 0.1% (w/v) sodium chloride, measured with the described method. This suggests a physical change of the buffer system. It is known that with the temperature sinking, sodium monohydrogen phosphate preferably crystallises from aqueous phosphate-buffered solutions and thus causes this change in pH.

Aqueous preparations of rViscumin have already been described in EP 0 751 221B 1. These aqueous preparations which are suitable as medicaments are aqueous solutions buffered with phosphate pH 7.2 and a rViscumin concentration of 100-200 ng/ml and, e.g., have the following composition:

| | |
|---|---|
| rViscumin | 100 ng |
| Sodium monohydrogenphosphate dihydrate | 3.56 mg |
| Sodium dihydrogenphosphate dihydrate | 0.64 mg |
| Sodium chloride | 67.0 mg |
| Poly(1-vinyl-2-pyrrolidone) K 17 | 0.5 mg |
| Water for injection purposes | ad 1 ml. |

When cooling down and freezing, phosphate buffers pH 7.2 show a decrease in the pH value which is due to the sinking temperature as has also been measured for phosphate buffer pH 8.0 and as has been described in FIG. 1. It is known to the person skilled in the art that low initial values of the pH upon freezing the aqueous solution lead to stronger shifts into the acid range as the concentration of sodium dihydrogenphosphate in the solution is increased. If preparations of the above-mentioned composition are lyophilised this inevitably leads to low pH conditions below pH 6, under which rViscumin is not stable and losses in activity occur due to the denaturation of the protein, as has been depicted for aqueous rViscumin preparations in FIG. 5.

The pH courses of the biological buffers TRIS/HCl, TRION/HCl and Hepes/HCl pH 8.0 are shown and discussed in Gloger O., Müller B. W., 2000.

With a decreasing temperature, buffer systems consisting of TRIS/HCl, TRISIN/HCl and Hepes/HCl adjusted to the pH value 8.0 show a continuous low change in pH to larger pH values up to 9.0 (Gloger O., Müller B. W., 2000).

EXAMPLE 2

Stability of Carbohydrate-Specific rViscumin Depending on the pH Value and Short-Time Storage rViscumin in a concentration of 200 ng/ml is solved in different buffers. Starting from a 20 mM phosphate buffer (pH 7.4) buffers with the pH values 3, 4, 5, 7, 8 and 9 are produced with NaOH (1M and 0.1M) or HCl (10% or 1%). Moreover, the phosphate-buffered solutions contain NaCl in a final concentration of 0.7 to 0.9% for adjusting the isotonicity of the solution and low-molecular polyvinylpyrrolidone in a concentration of 0.1 g/l for preventing an adsorption of the polypeptide to the surface of the vessel. The solutions are filtered for germs over a membrane (pore size 0.2 μm) and are stored in closed polyethylene containers under controlled temperature conditions at 2 to 8° C. Depending on the time, samples are taken. These samples are diluted 1:10 with 20 mM phosphate buffer (pH 7.4) in order to obtain uniform solutions for the determination of the protein content with lectin activity by means of a specific enzyme-coupled immunoassay using a glycoprotein and a specific monoclonal antibody. Example 4 describes an example for an assay for the determination of the protein content of a solution with lectin activity.

The assay shown in FIG. 2 indicates that the stability of the polypeptide rViscumin decreases markedly in the buffered solutions with decreasing pH value. Below a pH value of pH 6, no more rViscumin with lectin activity is left in the solutions after a short storage period. The highest stability of rViscumin while keeping the lectin activity is observed at high pH values.

EXAMPLE 3

Stability of rViscumin (rML) Lyophilisation Product rViscumin in a concentration of 2.0 μg/ml is solved in a buffered, stabilised solution containing 200 mM Tris/HCl buffer (pH 8.0), 8.0% (w/v) dextrane T10, 0.1% (w/v) NaCl and 0.1% (w/v) Polysorbate 80. Part of this solution is transferred under aseptic conditions by lyophilisation into a powder. To this avail, after filtration for germs, 0.5 ml of the solution is filled into glass vials through a 0.2 μm filter, is partly closed with a lyophilisation plug and is dried in a lyophiliser. The other part is also filtered for germs, filled into glass vials and is closed and stored until examination at 2 to 8° C.

After lyophilisation the glass vials with the aqueous solution as well as those with the solid (dried solution) are placed into a controlled water bath with a temperature and time control. The glass vials were subjected to the following temperatures:

5 minutes at 30° C.
heating with a temperature increase of 1.5° C./minute
5 minutes at 40° C.
heating with a temperature increase of 1.5° C./minute
5 minutes at 50° C.
heating with a temperature increase of 1.5° C./minute
5 minutes at 60° C.

After adjusting the temperature, the protein content with lectin activity in the selected samples of the solution and of the solid was determined by means of a specific enzyme-coupled immunoassay by using a glycoprotein and a specific monoclonal antibody. An example of an assay for the determination of the protein content of a solution with lectin activity is described in example 4.

The assay shown in FIG. 3 shows that the content of rViscumin in the buffered stabilised solution decreases markedly starting at a temperature of 40° C. At 50° C., only 50% of the initial concentration of rViscumin with lectin activity are detected. After heating the solution to 60° C., it is no longer possible to find rVisumin with lectin activity. Thus, the disintegration temperature of rViscumin in solution lies between 40° C. and 50° C.

The content of rViscumin with lectin activity in the solid only decreases very slowly as the temperature increases. At a temperature of 50° C., a content of 94% and at 60° C., a content of 91% of the initial content of rViscumin with lectin activity is found. This shows that rVisumin is much more stable in the lyophilised powder than in the solution.

EXAMPLE 4

Determination of the Protein Content of a Solution with Lectin Activity

100 µl of a solution of 0.1 mg/ml Asialofetuin in carbonate buffer pH 9.6 are placed in the wells of a 96 microtiter plate with a high protein binding and are incubated for 16 hours at ambient temperature. After washing three times with PBS containing 0.05 g/l Polysorbate 80, the wells of the microtiter plate are incubated for 1 hour at ambient temperature with 200 µl PBS containing 10 g/l bovine serum albumin and 0.05 g/l polysorbate 80 (blocking of unspecific binding sites). After washing three times, 100 µl of the rViscumin reference solution in the concentration range of 10-200 ng/ml, 100 µl of the test solution and for the determination of the blank reading 100 µl of the buffer (PBS with 0.05 g/l Polysorbate 80), respectively, are placed into the wells and are incubated at ambient temperature for two hours. Afterwards, the wells of the microtiter plate are washed and 100 µl of a solution of a specific monoclonal detection antibody (anti-rViscumin A-chain IgG of mouse) in a concentration of 1 µg/ml in PBS containing 0.05 g/l Polysorbate 80 and 0.1 g/l bovine serum albumine are added and incubated at ambient temperature for 1 hour. The wells of the microtiter plates are washed three times and 100 µl of a specific commercially available peroxidase (POD)-coupled anti-IgG-mouse antibody in the dilution according to the indications of the supplier are added and are incubated at ambient temperature for 1 hour. The wells of the microtiter plate are washed six times and subsequently 100 µl of a solution of a commercially available ortho-phenylenediamine/$H_2O_2$ tablet in 25 ml citrate buffer pH 5 are added and are incubated in the dark at room temperature for 15 minutes. After 15 minutes 100 µl of a 1M sulphuric acid are added to each well and the intensity of the colouration of the solution is determined by absorption measurement.

The content in the test solutions is determined in comparison with the reference solutions.

EXAMPLE 5

Dextrane-Containing rViscumin Injection Solution 10 µg/ml (Lyophilisation Product)

In the following, different formulae for dextrane-containing injection solutions are described.

To this avail, Polysorbate, Tris base and dextrane were solved in 80% of the amount of water necessary for injection purposes. Subsequently, the pH is adjusted to 8.0 with HCl (1N). rViscumin is added to this solution and is stirred well. The residual water is used to fill up to the required set volume. Subsequently, the solution is sterile filtered over a 0.2 µm filter. The solution is filled into glass vials under aseptic conditions, is pre-closed with the lyophilisation plug and is dried in the lyophiliser.

| Formula with dextrane T1 | |
|---|---|
| rViscumin | 0.01 mg |
| Polysorbate 80 | 1 mg |
| Tris base | 24.2 mg |
| HCl (1N) | q.s. pH 8.0 |
| Dextrane T1 | 80 mg |
| Water for injection purposes | ad 1.0 ml |

Moreover, in the following the preparation of a rViscumin injection solution is described which additionally comprises NaCl. The latter is solved in water together with polysorbate, tris base and dextrane.

| Formula with dextrane T1 and NaCl | |
|---|---|
| rViscumin | 0.01 mg |
| Polysorbate 80 | 1 mg |
| Tris base | 24.2 mg |
| HCl (1N) | q.s. pH 8.0 |
| NaCl | 1 mg |
| Dextrane T1 | 80 mg |
| Water for injection purposes | ad 1.0 ml |

The last example of this group of rViscumin preparations moreover describes the preparation of an rViscumin injection solution which also comprises Na-EDTA in addition to NaCl. These are solved in water simultaneously with polysorbate, Tris base and dextrane.

| Formula with dextrane T1, NaCl and Na-EDTA | |
|---|---|
| rViscumin | 0.01 mg |
| Polysorbate 80 | 1 mg |
| Tris base | 24.2 mg |
| HCl (1N) | q.s. pH 8.0 |
| Di-sodium-EDTA | 0.01 mg |
| NaCl | 1 mg |

-continued

| Formula with dextrane T1, NaCl and Na-EDTA | |
|---|---|
| Dextrane T1 | 80 mg |
| Water for injection purposes | ad 1.0 ml |

In the examples shown, for the reconstruction of the lyophilisation products, each of these is taken up in the amount of water indicated.

EXAMPLE 6

β-HP-Cyclodextrine-Containing rViscumin Injection Solution 10 μg/ml (Lyophilisation Product)

| Formula with β-HP-cyclodextrine | |
|---|---|
| rViscumin | 0.01 mg |
| Polysorbate 80 | 1 mg |
| Tris base | 24.2 mg |
| HCl (1N) | q.s. pH 8.0 |
| Di-sodium-EDTA | 0.01 mg |
| β-HP-cyclodextrine | 80 mg |
| Water for injection purposes | ad 1.0 ml |

For the preparation of this injection solution, polysorbate, Tris base, di-sodium edetine acid and β-hydroxypropyl-cyclodextrine are solved in 80% of the amount of water necessary for injection purposes. Subsequently, the pH is adjusted to 8.0 with HCl (1 N). rViscumin is added to this solution and is stirred well. The residual water is used to fill up to the required set volume. Subsequently, the solution is sterile filtered over a 0.2 μm filter. The solution is filled into glass vials under aseptic conditions, is pre-closed with the lyophilisation plug and is dried in the lyophiliser.

EXAMPLE 7

Aqueous rViscumin Solution 10 μg/ml Containing Amino Acids (Lyophilisation Product)

The production of the solutions is carried out according to the process as described in example 4. Accordingly, polysorbate, Tris base, sodium chloride and the amino acid(s) are solved in 80% of the amount of water necessary for injection purposes. The solutions are filled into glass ampouls or glass bottles under aseptic conditions. The medicament is stable under storage conditions of 2 to 8° C.

| Formula with glutamic acid | |
|---|---|
| rViscumin | 0.01 mg |
| Polysorbate 80 | 1 mg |
| Tris base | 2.4 mg |
| HCl (1N) | q.s. pH 8.0 |
| NaCl | 6.5 mg |
| Glutamic acid | 0.1 mg |
| Water for injection purposes | ad 1.0 ml |

| Formula with glutamic acid and valin | |
|---|---|
| rViscumin | 0.01 mg |
| Polysorbate 80 | 1 mg |
| Tris base | 2.4 mg |
| HCl (1N) | q.s. pH 8.0 |
| NaCl | 6.5 mg |
| Glutamic acid | 0.1 mg |
| Valine | 10 mg |
| Water for injection purposes | ad 1.0 ml |

If 80 mg dextrane T1 is added to the solutions prior to filling them up, lyophilisation products, too, can be prepared.

EXAMPLE 8

Influence of Different Amino Acids on the Stability of Carbohydrate-Specific rViscumin in Buffered Saline Solutions In the description it is shown that representatives of the amino acids with acidic, neutral and basic properties are able to stabilise the polypeptide rViscumin in aqueous, buffered solutions.

The assay summarised in the following table clarifies the influence of amino acids on the stabilisation of rViscumin in buffered, aqueous, saline solutions at a pH value of 8.0.

| Amino acid | Concentration mg/ml | Content (%) Initial value | Content (%) 3 days storage |
|---|---|---|---|
| no | — | 100% | 21.7% |
| glutamic acid | 0.1 | 100% | 100% |
| | 10 | 100% | 100% |
| valine | 0.1 | 100% | 24.2% |
| | 10 | 100% | 91.3% |
| arginine | 0.1 | 100% | 74.2% |
| | 10 | 100% | 30.5% |

If an rViscumin solution is stored for three days at 2 to 8° C., 22% of the carbohydrate-specific rViscumin can still be detected after this period of time.

If, however, the acidic amino acid glutamic acid, which was here used as an example of an acidic amino acid, is added to the solution, 100% of the carbohydrate-specific polypeptide rViscumin can be recovered after three days of corresponding storage. This stabilising effect is observed in a concentration ranging from 0.1 to 10 mg/ml.

If neutral amino acids such as e.g. valine are added, a stabilisation of the polypeptides in the aqueous solution can be observed, too. With respect to this amino acid, the concentration range which has a stabilising effect is at 10 mg/ml. After three days of storage, 91% of the initial content of rViscumin is still found.

Surprisingly, also with respect to the amino acids with basic properties in the low concentration range of 0.1 mg/ml, a stabilising effect on the protein could be observed. The recovery of the protein in the corresponding solution with a content of 74% is clearly above the content observed in the control preparation amounting to 22%.

Thus, as additives, amino acids have a stabilising effect on aqueous solutions and also as additives in dry preparations (powder, lyophilisation product) of rViscumin.

EXAMPLE 9

Aqueous rViscumin Solution, Concentration to Infusion 200 µg

An example of the preparation of a solution or of a concentrate of rViscumin for infusion is described in the following:

| Formula with glutamic acid | |
|---|---|
| rViscumin | 0.20 mg |
| Polysorbate 80 | 10 mg |
| Tris base | 24.1 mg |
| HCl (1N) | q.s. pH 8.0 |
| NaCl | 65 mg |
| Glutamic acid | 1 mg |
| Water for injection purposes | ad 10 ml |

The production of the solution is carried out according to the procedure as described in example 4. Accordingly, polysorbate, Tris base, sodium chloride and glutamic acid are solved in 80% of the required amount of water for injection purposes. Subsequently, the pH is adjusted to 8.0 with the help of HCl (1N). rViscumin is added to this solution and is stirred well. The residual water is used to fill up to the required set volume and the solution is sterile filtered over a 0.2 µm filter. The solution is filled into glass bottles under aseptic conditions. The medicament is stable under storage conditions of 2-8° C.

If 800 mg dextrane T1 is added to the solution prior to filling, it is also possible to produce a lyophilisation product.

EXAMPLE 10

Aqueous rViscumin Instillation Solution 500 µg

An example of the production of a solution of rViscumin for the installation in a body cavity is described in the following:

| Formula with glutamic acid | |
|---|---|
| rViscumin | 0.5 mg |
| Polysorbate 80 | 500 mg |
| Tris base | 121.1 mg |
| HCl (1N) | q.s. pH 8.0 |
| NaCl | 350 mg |
| Glutamic acid | 5 mg |
| Water for injection purposes | ad 50 ml |

The production of the solution is carried out according to the procedure as described in example 4. Accordingly, polysorbate, Tris base, sodium chloride and glutamic acid are solved in 80% of the required amount of water for injection purposes. Subsequently, the pH is adjusted to 8.0 with the help of HCl (1 N). rViscumin is added to this solution and is stirred well. The residual water is used to fill up to the required set volume and the solution is sterile filtered over a 0.2 µm filter. The solution is filled into glass bottles under aseptic conditions. The medicament is stable under storage conditions of 2-8° C.

If 2.0 mg dextrane T1 is added to the solution prior to filling, it is also possible to produce a lyophilisation product.

EXAMPLE 11

Glucose-Containing rViscumin Solution 10 µg/ml (Lyophilisation Product)

As described above, in a preferred embodiment of the invention sugar is added to the rViscumin solution. An example of the production of such a solution, which is subsequently lyophilised, is described in the following:

| Formula with glucose and NaCl | |
|---|---|
| rViscumin | 0.01 mg |
| Polysorbate 80 | 1 mg |
| Tris base | 24.2 mg |
| HCl (1N) | q.s. pH 8.0 |
| NaCl | 1 mg |
| Glucose | 80 mg |
| Water for injection purposes | ad 1.0 ml |

Polysorbate, Tris base and glucose are solved in 80% of the required amount of water for injection purposes. Subsequently, the pH is adjusted to 8.0 with the help of HCl (1N). rViscumin is added to this solution and is stirred well. The residual water is used to fill up to the required set volume and the solution is sterile filtered over a 0.2 µm filter. The solution is filled into glass vials under aseptic conditions, is preliminarily closed with the lyophilisation plug and is dried in the lyophilisation unit.

EXAMPLE 12

Sorbitol-Containing rViscumin Solution 10 µg/ml (Lyophilisation Product)

As is also described above, in other preferred embodiments of the invention sorbitol is added to the rViscumin solution. An example of the production of such a solution, which is subsequently lyophilised, is described in the following:

| Formula with sorbitol and NaCl | |
|---|---|
| rViscumin | 0.01 mg |
| Polysorbate 80 | 1 mg |
| Tris base | 24.2 mg |
| HCl (1N) | q.s. pH 8.0 |
| NaCl | 1 mg |
| Sorbitol | 80 mg |
| Water for injection purposes | ad 1.0 ml |

Polysorbate, Tris base and sorbitol are solved in 80% of the required amount of water for injection purposes. Subsequently, the pH is adjusted to 8.0 with the help of HCl (1N). rViscumin is added to this solution and is stirred well. The residual water is used to fill up to the required set volume. Subsequently, the solution is sterile filtered over a 0.2 µm filter. The solution is filled into glass vials under aseptic conditions, is preliminarily closed with the lyophilisation plug and is dried in the lyophilisation unit.

EXAMPLE 13

Chitosan-Containing rViscumin Solution 10 μg/ml (Lyophilisation Product)

| Formula with chitosan and NaCl | |
|---|---|
| rViscumin | 0.01 mg |
| Polysorbate 80 | 1 mg |
| Tris base | 24.2 mg |
| HCl (1N) | q.s. pH 8.0 |
| NaCl | 1 mg |
| Chitosan (low-molecular) | 80 mg |
| Water for injection purposes | ad 1.0 ml |

Polysorbate, Tris base and chitosan are solved in 80% of the required amount of water for injection purposes. Subsequently, the pH is adjusted to 8.0 with the help of HCl (1N). rViscumin is added to this solution and is stirred well. The residual water is used to fill up to the required set volume. Subsequently, the solution is sterile filtered over a 0.2 μl filter. The solution is filled into glass vials under aseptic conditions, is preliminarily closed with the lyophilisation plug and is dried in the lyophilisation unit.

EXAMPLE 14

Aerosil-Containing rViscumin Solution 100 μg/ml (Lyophilised Culture)

| Formula with silicum dioxide | |
|---|---|
| rViscumin | 0.1 mg |
| Polysorbate 80 | 10 mg |
| Tris base | 24.2 mg |
| HCl (1N) | q.s. pH 8.0 |
| Silicium dioxide (colloidal) | 20 mg |
| Dextrane T1 | 60 mg |
| Water for injection purposes | ad 1.0 ml |

Polysorbate, Tris base and dextrane are solved in 80% of the required amount of water for injection purposes. Subsequently, the pH is adjusted to 8.0 with the help of HCl (1N). rViscumin and the colloidal silicium dioxide is added to this solution and is stirred well. The residual water is used to fill up to the required set volume. The solution is filled into glass vials, is preliminarily closed with the lyophilisation plug and is dried in the lyophilisation unit.

EXAMPLE 15

Povidone-Containing rViscumin Solution 10 μg/ml (Lyophilisation Product)

| Formula with polyvinylpyrrolidone and NaCl | |
|---|---|
| rViscumin | 0.01 mg |
| Polysorbate 80 | 1 mg |
| Tris base | 24.2 mg |
| HCl (1N) | q.s. pH 8.0 |
| NaCl | 1 mg |
| Polyvinylpyrrolidone K17 | 80 mg |
| Water for injection purposes | ad 1.0 ml |

Polysorbate, Tris base and polyvinylpyrrolidone are solved in 80% of the required amount of water for injection purposes. Subsequently, the pH is adjusted to 8.0 with the help of HCl (1 N). rViscumin is added to this solution and is stirred well. The residual water is used to fill up to the required set volume. Subsequently, the solution is sterile filtered over a 0.2 μm filter. The solution is filled into glass vials under aseptic conditions, is preliminarily closed with the lyophilisation plug and is dried in the lyophilisation unit.

EXAMPLE 16 rViscumin Powder for the Preparation of a Solution, 10 mg rViscumin Solution for Oral Uptake Examples of the preparation of rViscumin powder, further processed for the subsequent oral application as powder and resolved in water prior to application are described in the following:

| Formula with dextrane | |
|---|---|
| 1. rViscumin | 10 mg |
| 2. Polysorbate 80 | 100 mg |
| 3. Tris base | 24 mg |
| 4. HCl (1N) | q.s. pH 8.0 |
| 5. Dextrane T1 | 10 g |
| 6. Sucrose | 10 g |

Positions 1 to 4 and parts of 5 (dextrane T1 serve as lyoprotective substance in this formula) are solved with purified water to 10 ml and are processed into a powder by lyophilisation. This powder is storable. As in the above-identified examples, the powder is mixed with the other substances and is filled into 100 ml bottles. In order to prepare the solution, the solid is solved with water to 100 ml.

Positions 1 to 5 and parts of 6 (sucrose serves as lyoprotective substance in this formula) of the following formula are solved with purified water to 10 ml and are processed into a powder by lyophilisation. This powder is storable. As in the above-identified examples, the powder is mixed with the other substances and is filled into 100 ml bottles. In order to prepare the solution, the solid is solved with water to 100 ml.

| Formula with sucrose | |
|---|---|
| 1. rViscumin | 10 mg |
| 2. Polysorbate 80 | 100 mg |
| 3. Tris base | 120 mg |
| 4. Glutamic acid | 10 mg |
| 5. HCl (1N) | q.s. pH 8.0 |
| 6. Sucrose | 10 g |
| 7. Flavours | 0.1 mg |
| 8. Sorbitol | 10 mg |
| 9. Water | ad 100 ml |

EXAMPLE 17 rViscumin Powder for the Preparation of a Solution, 10 mg rViscumin Juice for Oral Uptake An example of the preparation of rViscumin powder, further processed for a subsequent oral application as powder for the preparation of a juice and resolved in water prior to application is described in the following:

| Formula with sucrose | |
|---|---|
| 1. rViscumin | 10 mg |
| 2. Polysorbate 80 | 100 mg |
| 3. Tris base | 24 mg |
| 4. HCl (1N) | q.s. pH 8.0 |
| 5. Sucrose | 25 g |
| 6. Hydroxyethyl cellulose 400 | 700 mg |
| 7. Xanthane gum | 300 mg |
| 8. Flavours | 0.1 mg |
| 9. Glycerine 85% | 1 g |
| 10. Sorbitol | 10 g |

Positions 1 to 4 and parts of 5 are solved with purified water to 10 ml and are processed into a powder by lyophilisation. This powder is storable. In a known manner, the powder is mixed with the other substances and is filled into 100 ml bottles. In order to prepare the juice, the solid is filled up with water to 100 ml and is solved. After the swelling time has been observed, the juice is suitable for uptake.

EXAMPLE 18 rViscumin Tablets 0.1/0.5 mg 250 mg Tablet for Oral Uptake
Examples of the preparation of rViscumin tablets are shown in the following:

| Formula with dextrane/cellulose | | |
|---|---|---|
| 1. rViscumin | 0.1 mg | 0.5 mg |
| 2. Soy lecithin | 10 mg | 10 mg |
| 3. Tris base | 24 mg | 24 mg |
| 4. HCl (1N) | q.s. pH 8.0 | q.s. pH 8.0 |
| 5. Dextrane T1 | 100 mg | 100 mg |
| 6. Cellulose, microcrystalline | 99 mg | 99 mg |
| 7. Highly disperse silicium dioxide (Aerosil) | 5 mg | 5 mg |
| 8. Cross-linked polyvinylpyrrolidone (Kollidon CL) | 5 mg | 5 mg |
| 9. Magnesium stearate | 1 mg | 1 mg |

Positions 1 to 5 are solved with purified water to 2 ml and are processed into a powder by lyophilisation. This powder is storable. In a known manner, the powder is mixed with the other substances to form the powder which is pressed into tablets. These tablets can be coated with a common varnish which prevents the release of the active agent in the stomach (retarded release).

| Formula with sorbitol | | |
|---|---|---|
| 1. rViscumin | 0.1 mg | 0.5 mg |
| 2. Polysorbate 80 | 10 mg | 10 mg |
| 3. Tris base | 24 mg | 24 mg |
| 4. HCl (1N) | q.s. pH 8.0 | q.s. pH 8.0 |
| 5. Sorbitol | 200 mg | 200 mg |
| 6. Highly disperse silicium dioxide (Aerosil) | 5 mg | 5 mg |
| 8. Sodium carboxymethyl cellulose (Tylopur) | 5 mg | 5 mg |
| 9. Magnesium stearate | 1 mg | 1 mg |

Positions 1 to 4 and a part of 5 are solved with purified water to 2 ml and are processed into a powder by lyophilisation. This powder is storable. In a known manner, the powder is mixed with the other substances to form the powder which is pressed into tablets. These tablets can be coated with a common varnish which prevents the release of the active agent in the stomach (retarded release).

| Formula with dextrane | | |
|---|---|---|
| 1. rViscumin | 0.1 mg | 0.5 mg |
| 2. Polysorbate 80 | 5 mg | 5 mg |
| 3. Tris base | 12 mg | 12 mg |
| 4. HCl (1N) | q.s. pH 8.0 | q.s. pH 8.0 |
| 5. Dextrane T1 | 40 mg | 40 mg |
| 6. Cellulose, microcrystalline | 57 mg | 57 mg |
| 7. Highly disperse silicium dioxide (Aerosil) | 5 mg | 5 mg |

Positions 1 to 5 are solved with purified water to 1 ml and are processed into a powder by lyophilisation. This powder is storable. In a known manner, the powder is mixed with the other substances to form the powder which is filled into hard gelatine capsules.

EXAMPLE 19 rViscumin Suppository 1 mg

250 Suppository for Introduction into the Intestine
An example of the preparation of rViscumin suppositories is shown in the following:

| Formula with β-HP-Cyclodextrine | |
|---|---|
| 1. rViscumin | 1 mg |
| 2. Soy lecithin | 100 mg |
| 3. Tris base | 24 mg |
| 4. HCl (1N) | q.s. pH 8.0 |
| 5. Disodium EDTA | 10 mg |
| 6. β-HP-Cyclodextrine | 160 mg |
| 7. Sodium stearate | 50 mg |
| 8. Macrogol 300 | 250 mg |
| 9. Glycerol 85% | 1.9 g |
| 10. Purified water | ad 2.5 g |

Positions 1 to 6 are solved with purified water to 2 ml and are processed into a powder by lyophilisation. This powder is storable. In a known manner, the powder is mixed with the other substances to form a suppository. The admixing of rViscumin powder solved in a mixture of purified water and glycerol 85% into the suppository matrix is carried out at a controlled temperature. The mass is pressed into forms and is left to solidify by cooling.

EXAMPLE 20 rViscumin Gel 1 mg

Hydrophilic Gel for Dermal Application without Conservation

An example of the preparation of a hydrophilic rViscumin gel for dermal application is shown in the following:

| Formula with β-HP-Cyclodextrine | |
|---|---|
| 1. rViscumin | 1 mg |
| 2. Poloxamer 166 | 100 mg |
| 3. Tris base | 24 mg |
| 4. HCl (1N) | q.s. pH 8.0 |
| 5. Disodium EDTA | 10 mg |
| 6. β-HP-Cyclodextrine | 160 mg |
| 7. Sorbitan monostearate (Arlacel 60) | 200 mg |
| 8. Macrogol-9-stearate | 300 mg |
| 9. Glycerol 85% | 500 mg |
| 10. Medium-chain triglycerides | 500 mg |
| 11. Purified water | ad 10 g |

Positions 1 to 6 are solved with purified water to 2 ml and are processed into a powder by lyophilisation. This powder is storable. In a known manner, the powder is mixed with the other substances to form a gel. The admixing of rViscumin powder solved in purified water into the gel matrix is carried out at a temperature of below 30° C. If necessary, a conservation can be carried out with sodium benzoate or PHB esters.

EXAMPLE 21 rViscumin Powder for Inhalation 0.1/0.5 mg 1 g Powder

| Formula with dextrane/cellulose | | |
|---|---|---|
| 1. rViscumin | 0.1 mg | 0.5 mg |
| 2. Polysorbate 80 | 10 mg | 10 mg |
| 3. Tris base | 24 mg | 24 mg |
| 4. HCl (1N) | q.s. pH 8.0 | q.s. pH 8.0 |
| 5. Dextrane T1 | 100 mg | 100 mg |
| 6. Cellulose, microcrystalline | 860 mg | 860 mg |
| 7. Sodium carboxymethyl cellulose | 5 mg | 5 mg |

Positions 1 to 5 are solved with purified water to 2 ml and are processed into a powder by lyophilisation. This powder is storable. In a known manner, the powder is mixed with the other substances to form a powder, micronised and is administered by means of dry powder inhalators.

EXAMPLE 22

Influence of Selected Cryoprotectors on the Stability of rViscumin

Preparations of rViscumin with the following composition:

| | |
|---|---|
| rViscumin | 10 µg |
| Tris base | 12.1 mg |
| Hydrochloric acid 1N for adjustment of the | pH to 8.0 |
| Cryoprotector | 1/10 mg |
| Sodium EDTA | 10 µg |
| Water for injection purposes | ad 1 ml | are filled to 0.5 ml into freeze vials and are cooled down to −35° C. in the lyopiliser at a cooling down rate of 3K/hour, subsequently thawed and the carbohydrate-binding activity of rViscumin in the solution is determined according to the method as explained in example 4. Pluronic F68 and Polysorbate 80 are used as cryoprotectors.

After thawing, a recovery of the rViscumin activity in the range of 98 to 102% for both cryoprotectors in the two concentrations is found (FIG. 6).

The two cryoprotectors Pluronic F68 and Polysorbate 80 are suitable for stabilising rViscumin during freezing in the lyophilisation process in the preferred range, as shown for the two concentrations 0.1 to 1.0%,

EXAMPLE 23

Influence of the Protein Concentration on the Stability During Lyophilisation Preparations of rViscumin with the following composition:

| | |
|---|---|
| rViscumin | 10/50/100 µg |
| Tris base | 12.1 mg |
| Hydrochloric acid 1N for adjustment of the | pH to 8.0 |
| Polysorbate 80 | 1 mg |
| Sodium EDTA | 10 µg |
| Water for injection purposes | ad 1 ml | are filled to 0.5 ml into freeze vials and are cooled down to −35° C. in the lyopiliser at a cooling down rate of 3K/hour and are subsequently dried.

Drying Programme:

Primary drying: 8 hours at −10° C. and 80 kPa pressure followed by an increase in temperature to 10° C. during 8 hours and 80 kPa pressure, secondary drying: 6 hours at 30° C. and 10 kPa pressure.

When exclusively using the cryoprotector polysorbate 80, which is suitable for the stabilisation of rViscumin during the freezing process, the selected preparations with the different concentrations of rVicumin show an insufficient stabilisation of the protein after the termination of the lyophilisation process (FIG. 7). The stability of rVisumin in the lyophilisation product on the selection of the final concentration in the aqueous solution. Thus, the recovery of the activity increases from 50% for the concentration 10 µg/ml to 80% for the concentration 100 µg/ml. The example clearly shows that in all rViscumin concentrations the addition of suitable lyoprotectors has an advantageous effect on the stability of the lyophilised forms of medicaments.

EXAMPLE 24

Influence of Mannitol (Mannite) and Mannitol/Dextrane on the Stability of rViscumin The preparations of rViscumin (10 µg/ml) with the following composition

| Solution | Mannite | Mannite/dextrane |
| --- | --- | --- |
| rViscumin | 10 µg | 10 µg |
| Mannite | 20 mg | 20 mg |
| Dextrane T1 | | 20 mg |
| Tris base | 12.1 mg | 12.1 mg |
| Hydrochloric acid (1N) for the adjustement of the pH to 8.0 | | |
| Polysorbate 80 | 1 mg | 1 mg |
| Sodium EDTA | 10 µg | 10 µg |
| Water for injection purposes | ad 1 ml | ad 1 ml | are filled to 0.5 ml into freeze vials and are cooled down to −35° C. in the lyophiliser at a cooling down rate of 3K/hour and are subsequently dried.

Drying Programme:

Primary drying: 8 hours at −10° C. and 80 kPa pressure followed by an increase in temperature to 10° C. during 8 hours and 80 kPa pressure, secondary drying: 6 hours at 30° C. and 10 kPa pressure.

By adding mannite in a suboptimal concentration of 2%, a recovery activity for rViscumin of 61% is determined (FIG. 8). Marmite is suitable for the stabilisation of rViscumin as it can increase the stability of the lyophilised rViscumin solution 10 µg/ml of 50% to 61%. A mixture of mannite 2% and dextrane T1 2% results in a recovery of the activity of 74% after lyophilisation, which leads to the conclusion that dextrane alone can also have a positive effect on stability.

EXAMPLE 25

Influence of Dextrane T1 on the Stability of rViscumin

The preparations of rViscumin (10 µg/ml) with the following composition:

| | |
| --- | --- |
| rViscumin | 10 µg |
| Dextrane T1 | 0/8/20/40/80 mg |
| TRIS base | 12.1 mg |
| Hydrochloric acid (1N) for the adjustment of the | pH to 8.0 |
| Polysorbate 80 | 1 mg |
| Sodium EDTA | 10 µg |
| Water for injection purposes | ad 1 ml | are filled to 0.5 ml into freeze vials and are cooled down to −35° C. in the lyophiliser at a cooling down rate of 3K/hour and are subsequently dried.

Drying Programme:

Primary drying: 8 hours at −10° C. and 80 kPa pressure followed by an increase in temperature to 10° C. during 8 hours and 80 kPa pressure, secondary drying: 6 hours at 30° C. and 10 kPa pressure.

A recovery of 89% of the activity of rViscumin is detected for the suboptimal concentration of 2% dextrane T1. The stability of rViscumin with dextrane is significantly enhanced compared to the results obtained when the mixture mannite/dextrane was used. Beginning at a dextrane concentration larger than or equal to 4%, stable, solid pharmaceutical preparations are obtained in the lyophilisation process. Dextrane is suitable as lyoprotector for rViscumin.

EXAMPLE 26

Influence of Further Lyoprotectors

The preparations of rViscumin (10 µg/ml) with the following composition:

| | |
| --- | --- |
| rViscumin | 10 µg |
| Lyoprotector | 80 mg, except mannite 20 mg |
| TRIS base | 12.1 mg |
| Hydrochloric acid (1N) for adjustment of the | pH to 8.0 |
| Polysorbate 80 | 1 mg |
| Sodium EDTA | 10 µg |
| Water for injection purposes | ad 1 ml | are filled to 0.5 ml into freeze vials and are cooled down to −35° C. in the lyophiliser at a cooling down rate of 3K/hour and are subsequently dried.

Drying Programme:

Primary drying: 8 hours at −10° C. and 80 kPa pressure followed by an increase in temperature to 10° C. during 8 hours and 80 kPa pressure, secondary drying: 6 hours at 30° C. and 10 kPa pressure.

The suitability of the preparations with the lyoprotectors in concentrations of 8% hydroxyethyl starch 450 (HES 450 8%), of 8% β-hydroxypropylcyclodextrine ((3-HP-CD 8%), of 8% hydroxyethyl starch 130 (HES 130 8%) and of 8% dextrane T1 (TRIS 100 Dex T1 8%) and mannite in a concentration of 2% (w/v) (Man 2%) is evident. The preparations which have been cited first show a recovery of active rViscumin of above 60% after 8 hours at 60° C., while the preparation with mannite only exhibits a reduced stress stabililty under these conditions (FIG. 10).

The conditions for the distribution of medicaments can be derived from these data with respect to stress stability. Dried rViscumin medicaments do not have to be transported in a closed cooling chain, as is necessary for the aqueous preparations.

EXAMPLE 27

Comparative Storage Stability of rViscumin Solution and rViscumin Powder

The preparation of rViscumin (10 µg/ml) with the following composition:

| | |
| --- | --- |
| rViscumin | 10 µg |
| Dextrane T10 | 80 mg |
| TRIS base | 12.1 mg |
| Hydrochloric acid (1N) for adjustment of the | pH to 8.0 |
| Polysorbate 80 | 1 mg |
| Sodium EDTA | 10 µg |
| Water for injection purposes | ad 1 ml | are filled to 0.5 ml into freeze vials and are cooled down to −35° C. in the lyophiliser at a cooling down rate of 3K/hour and are subsequently dried.

Drying Programme:

Primary drying: 8 hours at −10° C. and 80 kPa pressure followed by an increase in temperature to 10° C. during 8 hours and 80 kPa pressure, secondary drying: 6 hours at 30° C. and 10 kPa pressure.

Subsequently, the vials are stored under controlled conditions at 2 to 8° C.

The preparation of rViscumin (1 µg/ml) with the following composition:

| | |
|---|---|
| rViscumin | 1 µg |
| Sodium monohydrogenphosphate dihydrate | 17.8 mg |
| Sodium dihydrogenphosphate dihydrate | 3.13 mg |
| Sodium chloride | 37.5 mg |
| Polyvidone K 17 | 1 mg |
| Sodium EDTA | 1 mg |
| Water for injection purposes | ad 1 ml | is filled into glass ampoules and is stored under controlled conditions at 2 to 8° C. This preparation is comparable to the aqueous pharmaceutical preparations of rViscumin described in EP 0 751 221B 1

After a storage period of 52 weeks, rViscumin shows an unchanged activity in the lyophilised powder. No loss in activity can be detected. The aqueous preparation corresponding to the state of the art only shows stability over a short storage period and after 6 weeks of storage it has only an activity of 70% (FIG. 11). The clear superiority of the lyophilised preparation is shown. From these data, longer durations than 1 year for the forms of medicaments of rViscumin in powder form can be concluded, while the aqueous preparation formulated according to the state of the art only has a shorter duration.

The examples given above explain the described invention.

Various documents are cited in the text of this description. The disclosure content of the cited documents (including all manufacturers' descriptions and indications etc.) is herewith incorporated in the description by reference.

LITERATURE

Allison S D, Chang B S, Randolph T W, Carpenter J F. Hydrogen Bonding between Sugar and Protein is Responsible for Inhibition of Dehydration-Induced Protein Unfolding. Arch Biochem Biophys., 1999; 365 (2): 289-299.

Allison S D, Manning M C, Randolph T W, Middleton K, Davis A, Carpenter J R Optimization of Storage Stability of Lyophilized Actin Using Combinations of Disaccharides and Dextran. J Pharm Sci., 2000; 89 (2) 199-214.

Bocci V; Mistletoe (Viscum album) lectins as cytokine inducers and immunoadjuvant in tumor therapy. J Biol Regul Homeost Agents, 1993; 7(1): 1-6.

Beuth I, Ko H L, Gabius H J, Pulverer G.; Influence of treatment with the immunomodulatory effective dose of the beta-galactoside-specific lectin from mistletoe on tumor colonization in BALB/c-mice for two experimental model systems. In Vivo, 1991; 5(1): 29-32.

Beuth J, Ko H L, Gabius H J, Burrichter H, Oette K, Pulverer G.; Behavior of lymphocyte subsets and expression of activation markers in response to immunotherapy with galactoside-specific lectin from mistletoe in breast cancer patients. Clin Investig., 1992; 70(8): 658-61.

Beuth J, Ko H L, Tunggal L, Geisel J, Pulverer G.; [Comparative studies on the immunoactive action of galactoside-specific mistletoe lectin. Pure substance compared to the standardized extract]. Arzneimittelforschung., 1993a; 43(2):166-9. German language.

Carpenter J F, Prestrelinski S J, Arakawa T.; Separation of Freezing- and Drying-Induced Denaturation of Lyophilized Proteins Using Stress-Specific Stabilisation: I. Enzyme Activity and calorimetric Studies. Arch Biochem Biophys., 1993; 2: 456-464.

Carpenter J K, Izutsu K; Freezing- and Drying-Induced Perturbations of Protein Structure and Mechanism of Protein Protection by Stabilizing Additives. in Rey L, May J C (eds); Freeze-Drying/Lyophilization of Pharmaceutical and Biological Products. New York, Basle: Marcel Dekker Inc. 1999: 123-160.

Dulat H J, von Grumbkow C, Baars W, Schroder N, Wonigeit K, Schwinzer R; Down-regulation of human alloimmune responses by genetically engineered expression of CD95 ligand on stimulatory and target cells. Eur J. Immunol., 2001; 31(7): 2217-26

Endo Y, Tsurugi K, Lambert J M.; The site of action of six different ribosomeinactivating proteins from plants on eukaryotic ribosomes; the RNA N-glycosidase activity of the proteins. Biochem Biophys Res Commun., 1988; 150 (3): 1032-6.

Endo Y, Oka T, Tsurugi K, Franz H.; The mechanism of action of the cytotoxic lectin from Phoradendron californicum: the RNA N-glycosidase activity of the protein. FEBS Left., 1989; 248(1-2): 115-8.

Franz H, Haustein B, Luther P, Kuropka U, Kindt A; Isolation and characterization of mistletoe extracts (Viscum album L.). I. Affinity chromatography of mistletoe extracts on immobilized plasma proteins. Acta Biol Med Ger., 1977, 36(1): 113-7.

Gabius H J, Walzel H, Joshi S S, Kruip J, Kojima S, Gerke V, Kratzin H, Gabius S.; The immunomodulatory beta-galactoside-specific lectin from mistletoe: partial sequence analysis, cell and tissue binding, and impact on intracellular biosignalling of monocytic leukemia cells. Anticancer Res., 1992; 12(3): 669-75.

Gabius H J, Gabius S, Joshi S S, Koch B, Schroeder M, Manzke W M, Westerhausen M.; From ill-defined extracts to the immunomodulatory lectin: will there be a reason for oncological application of mistletoe? Planta Med., 1994; 60(1): 2-7.

Gabius H J and Gabius S; Die Misteltherapie auf dem naturwissenschaftlichen Priffstand. PZ., 1994; 139, 9-16.

Ganguly C and Das S.; Plant lectins as inhibitors of tumour growth and modulators of host immune response. Chemotherapy, 1994; 40(4): 272-8.

Gerhardt, P, Murray, R G E, Wood, W A, Krieg, N R, (1994) "Methods for General and Molecular Bacteriology", American Society for Microbiology.

Gloger O., Müller B. W.; Influence of freezing on the pH-shift of different buffer systems. Proceedings 3$^{rd}$ World Meeting on Pharmaceutics, Biopharmaceutics and Pharmaceutical Technology 2000, 967-968

Hajto T. Immunomodulatory effects of iscador: a Viscum album preparation. Oncology, 1986; 43 Suppl 1: 51-65.

Hajto T, Hostanska K, Gabius H J. Modulatory potency of the beta-galactoside-specific lectin from mistletoe extract (Iscador) on the host defense System in vivo in rabbits and patients. Cancer Res., 1989; 49(17): 4803-8.

Hajto T, Hostanska K, Frei K, Rordorf C, Gabius H J.; Increased secretion of tumor necrosis factors alpha, interleukin 1, and interleukin 6 by human mononuclear cells exposed to beta-galactoside-specific lectin from clinically applied mistletoe extract. Cancer Res., 1990; 50(11): 3322-6.

Hajto, T, Hostanska, K, (2001); EP 0 602 686 B1

Heiny B M, Beuth J.; Mistletoe extract standardized for the galactoside-specific lectin (ML-1) induces Beta-endorphin release and immunopotentiation in breast cancer patients. Anticancer Res., 1994; 14(3B): 1339-42.
Lentzen, H, Eck, J, Baur, A, Zinke, H, (1998); EP 0 751 221B 1.
Mannel D N, Becker H, Gundt A, Kist A, Franz H.; Induction of tumor necrosis factor expression by a lectin from Viscum album. Cancer Immunol Immunother., 1991; 33(3): 177-82.
Matzinger P; The JAM test. A simple assay for DNA fragmentation and cell death. J Immunol Methods., 1991; 145 (1-2): 185-92.
Old, RW and Primrose, SB; (1992) "Gentechnologie, Eine Einftihrung" Georg Thieme Verlag Stuttgart New York.
Paques, EP; (1994) EP 0 430 200 B1.
Peumans W J, Hao Q, Van Damme E L; Ribosome-inactivating proteins from plants: more than RNA N-glycosidases? FASEB J., 2001; 15(9): 1493-506
Sambrook et al., (1989) "Molecular Cloning, A Laboratory Manual"; second edition, CSH Press, Gold Spring Harbor.
Woog, H, Gruber, W, Markl, H J, Demmer, F. (1992), EP 0 306 824 B1.
Woog, H, Gruber, W, Markl, H J, Winter, G, Demmer, F. (1996), EP 0 607 156 B 1.

The invention claimed is:

1. A method for the production of a medicament containing a polypeptide which is in stable form for storage for at least one year, and optionally contains a pharmaceutically acceptable carrier, said polypeptide comprising at least one recombinant carbohydrate-binding polypeptide that is the B-chain of a ribosome-inactivating protein or a functional fragment or derivative of said carbohydrate-binding polypeptide wherein said polypeptide comprises a polypeptide selected from the group consisting of
    (a) said carbohydrate binding polypeptide or a functional fragment or derivative of said carbohydrate binding polypeptide which is fused to a cytotoxically effective peptide to form a fusion protein;
    (b) said carbohydrate binding polypeptide or a functional fragment or derivative of said carbohydrate binding polypeptide which is linked to another polypeptide which has an enzymatic rRNA-N-glycosidase activity;
    (c) said carbohydrate binding polypeptide or a functional fragment or derivative of said carbohydrate binding polypeptide which is linked to another polypeptide in which an enzymatic rRNA-N-glycosidase activity has been replaced by another cytotoxic activity; and
    (d) said carbohydrate binding polypeptide or a functional fragment or derivative of said carbohydrate binding polypeptide, which is linked to a fusion protein, comprising a polypeptide with an enzymatic rRNA-N-glycosidase activity and/or another cytotoxic activity;
    comprising the step of cooling, freezing, spray drying or lyophilising while retaining the pharmacological properties of the polypeptide in the solution, wherein said solution has a pH value higher than pH 6.0 and a buffer system which maintains this pH-value, and a lyoprotector in a final concentration of between 4.0 and 10%, wherein said lyoprotector is a dextran.

2. The method of claim 1, wherein the further polypeptide which is linked to the recombinant carbohydrate-binding polypeptide is the A-chain of a ribosome-inactivating protein.

3. The method of claim 1, wherein the ribosome-inactivating protein is a ribosome-inactivating protein of the type II.

4. The method of claim 3, wherein the ribosome inactivating protein is a type II rViscumin.

5. The method of claim 1, wherein the pH-value of the solution is between 6.0 and 9.0.

6. The method of claim 1, wherein the pH-value of the solution is between 7.5 and 8.5.

7. The method of claim 1, wherein the salt(s) of the buffer system is/are used in a end concentration ranging from 5 mM to 200 mM.

8. The method of claim 1, wherein the salt(s) of the buffer system is/are used in an end concentration ranging from 100 mM to 200 mM.

9. The method of claim 1, wherein the salt(s) of the buffer system comprise one or more salts selected from the group consisting of TRIS/HCl, TRICIN/HCl, HEPES/HCl, ammonium carbonate buffer, TRIS/glutamic acid and TRIS/aspartic acid.

10. The method of claim 1, wherein the solution contains one or more surfactants in order to stabilise the pharmacological properties of the polypeptide.

11. The method of claim 10, wherein the surfactants are non-ionic tensides and are used in a final concentration ranging from 0.01 to 5.0%.

12. The method of claim 11, wherein the non-ionic tensides are selected from the group comprising: fatty alcohols, partial glycerides, polysorbates, polyoxyethylene fatty acid ethers and polyoxyethylene fatty acid esters, poloxamers (polyoxypropylene-polyoxyethylene-block polymers), saccharide fatty acid esters, polyoxyglycerol fatty acid esters and phosphatides.

13. The method of claim 12, wherein the polysorbates are selected from the group consisting of Polysorbate 80, Polysorbate 20 and polyoxyethylene sorbitol ether.

14. The method of claim 12, wherein the polyoxyethylene fatty acid ethers and polyoxyethylene fatty acid esters are macrogol ethers or macrogol esters.

15. The method of claim 12, wherein the poloxamer is Pluronic F68, or poloxamer 188.

16. The method of claim 12, wherein the phosphatides are lecithins.

17. The method of claim 10, wherein the surfactants are amphoteric tensides and are used in a final concentration ranging from 0.01 to 5.0%.

18. The method of claim 1, wherein dextran is added in a final concentration ranging from 4.0 to 10% and a cryoprotector is added in a final concentration ranging from 0.05 to 0.1%.

19. The method of claim 18, wherein ionic substances are used as cryoprotectors.

20. The method of claim 19, wherein the ionic substances are selected from the group consisting of sodium chloride, sodium sulphate, potassium chloride and potassium sulphate.

21. The method of claim 18, wherein the lyoprotectors and cryoprotectors form amorphous structures during lyophilisation.

22. The method of claim 1, wherein the solution contains one or more amino acids which are used in a final concentration of from 0.01 to 50 mg/ml.

23. The method of claim 22, wherein the amino acids are selected from the group comprising acidic amino acids such as glutamic acid and aspartic acid, the basic amino acid arginine and the neutral amino acid valine.

24. The method of claim 1, wherein the polypeptide comprising at least one recombinant carbohydrate-binding polypeptide or functional fragment or derivative of this polypeptide is used in a final concentration of from 10 ng/ml to 10 mg/ml.

25. The method of claim 24, wherein the polypeptide is used in a final concentration of from 100 ng/ml to 1 mg/ml.

26. The method of claim 1, moreover comprising the further formulation or reconstitution of the medicament as aqueous or non-aqueous solution.

27. The method of claim 26, wherein the medicament is further formulated as injection solution, instillation solution or infusion solution.

28. The method of claim 1, moreover comprising the further formulation or reconstitution of the medicament for gastrointestinal, oral, nasal, pulmonary, dermal, transdermal or local application.

29. The method of claim 1, moreover comprising the further formulation of the medicament into juice, capsules, tablets, suppositories or gels.

30. The method of claim 1, moreover comprising the further formulation of the medicament into a powder for inhalation which is administered by use of an inhalator.

31. A medicament, produced according to the method of claim 1.

* * * * *